(12) United States Patent
Zebala

(10) Patent No.: US 9,000,142 B2
(45) Date of Patent: Apr. 7, 2015

(54) PHOTOCLEAVABLE SENSE-ANTISENSE COMPLEX

(75) Inventor: John A. Zebala, Sammamish, WA (US)

(73) Assignee: Syntrix Biosystems, Inc., Auburn, WA (US)

( * ) Notice: Subject to any disclaimer, the term of this patent is extended or adjusted under 35 U.S.C. 154(b) by 718 days.

(21) Appl. No.: 12/489,434

(22) Filed: Jun. 23, 2009

(65) Prior Publication Data

US 2010/0105120 A1 Apr. 29, 2010

Related U.S. Application Data

(60) Provisional application No. 61/078,444, filed on Jul. 7, 2008.

(51) Int. Cl.
| | | |
|---|---|---|
| C07H 21/02 | (2006.01) | |
| C07H 21/04 | (2006.01) | |
| C12N 13/00 | (2006.01) | |
| C12N 15/11 | (2006.01) | |

(52) U.S. Cl.
CPC .............. *C12N 13/00* (2013.01); *C12N 15/111* (2013.01); *C12N 2310/14* (2013.01); *C12N 2310/318* (2013.01); *C12N 2310/3181* (2013.01); *C12N 2310/3233* (2013.01); *C12N 2310/344* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 6,017,758 | A | 1/2000 | Hazelton, III et al. |
| 6,242,258 | B1 | 6/2001 | Hazelton, III et al. |
| 6,410,327 | B2 | 6/2002 | Hazelton, III et al. |
| 2002/0155606 | A1 | 10/2002 | Okamoto |
| 2005/0059028 | A1 | 3/2005 | Ngugen et al. |
| 2005/0282203 | A1 | 12/2005 | Ngugen et al. |
| 2006/0008907 | A1* | 1/2006 | Friedman et al. ............. 435/455 |
| 2006/0292691 | A1* | 12/2006 | McSwiggen et al. ......... 435/325 |

OTHER PUBLICATIONS

Dmochoski et al., Taking control of gene expression with light-activated oligonucleotides. Biotechniques, 2007. 43(2): p. 161, 163, 165 passim.
Dussy et al., New light-sensitive nucleosides for caged DNA strand breaks. Chembiochem, 2002. 3(1): p. 54-60.
Mikat and Heckel, Light-dependent RNA interference with nucleobase-caged siRNAs. Rna, 2007.
Croock, Progress in Antisense Technology, Ann. Rev. Med. 55:61-95, 2004.
Nguyen et al., Light controllable siRNAs regulate gene suppression and phenotypes in cells. Biochim Biophys Acta, 2006. 1758(3): p. 394-403.
Shah et al. 1, Light-activated RNA interference. Angew Chem Int Ed Engl, 2005. 44(9): p. 1328-32.
Shah et al. 2, Tolerance of RNA Interference Toward Modifications of the 5☐ Antisense Phosphate of Small Interfering RNA , Oligonucleotides, 17:35-43, 2007.
Shestopalov et al., Light-controlled gene silencing in zebrafish embryos. Nat Chem Biol, 2007. 3(10): p. 650-1.
Tang 1, Controlling RNA Digestion by RNase H with a Light-Activated DNA Hairpin. Angew. Chem, 2006. 45:3523-3526.
Tang 2, Regulating gene expression with light-activated oligonucleotides. Mol Biosyst, 2007. 3(2): p. 100-10.
Tang 3 Regulating gene expression in human leukemia cells using light-activated oligodeoxynucleotides Nucleic Acids Res., 2007. 136:559-569.
Tang 4, Phototriggering of Caged Fluorescent Oligodeoxynucleotides Organic Letters 2005 7:279-282.
Tang 5 Photoregulation of DNA polymerase I (Klenow) with caged fluorescent oligodeoxynucleotides Bioorganic Medicinal Chemistry Letters, 2005 15:5503-5506.
Wagner Gene inhibition using antisense oligodeoxynucleotides, Nature 1994 372:333-335.

* cited by examiner

*Primary Examiner* — Amy Bowman
(74) *Attorney, Agent, or Firm* — Baker & Hostetler LLP

(57) ABSTRACT

There is disclosed a photocleavable sense-antisense nucleobase polymer complex capable of modulating gene expression comprising an unnatural antisense nucleobase polymer that targets an mRNA, and a photocleavable sense nucleobase polymer noncovalently bound to the antisense nucleobase polymer, wherein the photocleavable sense nucleobase polymer comprises a plurality of nucleobase polymers connected by a photocleavable linkage. There is also disclosed a method for controlling the time and spatial position of gene expression comprising selecting a target mRNA, introducing the photocleavable sense-antisense nucleobase polymer complex into a cell, and selectively irradiating the cell with light.

11 Claims, 6 Drawing Sheets

US 9,000,142 B2

SEQUENCE LISTING

<160> NUMBER OF SEQ ID NOS: 8

<210> SEQ ID NO 1
<211> LENGTH: 25
<212> TYPE: DNA
<213> ORGANISM: artificial sequence
<220> FEATURE:
<223> OTHER INFORMATION: zebra fish

<400> SEQUENCE: 1
aagttcttct cctttactca tggtg                                          25

<210> SEQ ID NO 2
<211> LENGTH: 25
<212> TYPE: DNA
<213> ORGANISM: artificial sequence
<220> FEATURE:
<223> OTHER INFORMATION: zebra fish

<400> SEQUENCE: 2
caccaugagu aaaggagaag aacuu                                          25

<210> SEQ ID NO 3
<211> LENGTH: 25
<212> TYPE: DNA
<213> ORGANISM: artificial sequence
<220> FEATURE:
<223> OTHER INFORMATION: zebra fish

<400> SEQUENCE: 3
aagttcttct cctttactca tggtg                                          25

<210> SEQ ID NO 4
<211> LENGTH: 25
<212> TYPE: DNA
<213> ORGANISM: artificial sequence
<220> FEATURE:
<223> OTHER INFORMATION: zebra fish

<400> SEQUENCE: 4
caccaugagu aaaggagaag aacuu                                          25

<210> SEQ ID NO 5
<211> LENGTH: 51
<212> TYPE: DNA
<213> ORGANISM: artificial sequence
<220> FEATURE:
<223> OTHER INFORMATION: zebra fish

<400> SEQUENCE: 5
ggggacaagt ttgtacaaaa aagcaccctc catgccgcag ccgaaaatcg c              51

<210> SEQ ID NO 6
<211> LENGTH: 50
<212> TYPE: DNA
<213> ORGANISM: artificial sequence
<220> FEATURE:
<223> OTHER INFORMATION: zebra fish

<400> SEQUENCE: 6
ggggaccact ttgtacaaga aagctgggtc catcatggag caggggcgtc                50

<210> SEQ ID NO 7
<211> LENGTH: 19
<212> TYPE: DNA
<213> ORGANISM: artificial sequence

```
<220> FEATURE:
<223> OTHER INFORMATION: zebra fish

<400> SEQUENCE: 7
cttctcaggc tgactgtgc                                                      19

<210> SEQ ID NO 8
<211> LENGTH: 18
<212> TYPE: DNA
<213> ORGANISM: artificial sequence
<220> FEATURE:
<223> OTHER INFORMATION: zebra fish

<400> SEQUENCE: 8
ccgctagcat taccctcc                                                       18
```

PHOTOCLEAVABLE SENSE-ANTISENSE COMPLEX

CROSS REFERENCE TO RELATED APPLICATIONS

The present patent application claims priority to U.S. provisional patent application 61/078,444 filed 7 Jul. 2008.

TECHNICAL FIELD

The present disclosure relates to light-activated gene expression. Provided is a photocleavable sense-antisense complex and methods for using such photocleavable sense-antisense complex for the spatio-temporal modulation of gene expression. In particular, methods are provided to precisely control, spatially and/or temporally, expression of a target mRNA.

BACKGROUND

There is a need in the art for spatiotemporal modulation of gene expression using targeted light to activate an antisense or RNA interference (RNAi) process within a cell. Fulfillment of such a need will have an important impact in functional genomics. This is particularly the case in transparent model organisms, such a zebrafish, *c. elegans* and *drosophila*. Irradiation can be specifically targeted visually to known anatomic landmarks (Dmochowski and Tang, *BioTechniques* 43(2):161, 2007). Irradiating selected organs or groups of cells within organs permits specific genes to be turned off at any time during the development of the organism and with cell-scale resolution, thereby permitting an in depth spatiotemporal understanding of the role of particular genes in the whole organism. Several photo-caging approaches have been employed to modify antisense and RNAi molecules to make them photoactivatable.

Investigators have used a hairpin design to control the activity of an antisense molecule, wherein the antisense molecule is covalently attached to a complementary sense molecule via a photocleavable linker. The sense and antisense molecules bind one another in a hairpin conformation, preventing the antisense molecule from binding to its target mRNA. Irradiation cleaves the linker and releases the antisense molecule, which dissociates from the complementary sense molecule and binds its target mRNA. Studies by Tang and Dmochowski in the zebrafish focused on negatively charged peptide nucleic acid (ncPNA) or phosphorothioate DNA (sDNA) as the antisense molecule, and 2'-OMe-RNA as the complementary sense molecule in the hairpin (Tang et al., *J. Am. Chem. Soc.* 129:11000, 2007). Their work in human leukemia cells employed both DNA and phosphorothioated DNA as both sense and antisense components (Tang et al., *Nucleic Acids Res.* 36(2):559, 2008). In contrast, Shestopalov et al. controlled gene expression in the zebrafish using a morpholino polymer to form both the antisense and sense components in the hairpin (Shestopalov et al., *Nature Chem. Biol.* 3(10):650, 2007). Hairpin approaches have also been described for siRNA (U.S. Patent Applications 2005/0059028 and 2005/0282203, the disclosure of which are incorporated by reference herein). An important limitation of the hairpin approach is the difficulty or significant synthetic chemistry expertise that is required to assemble the hairpin (Tang and Dmochowski, *Nature Protocols* 1(6):3041, 2006).

Other investigators have approached light control of gene expression by applying sterically encumbered photolabile blocking (i.e. caging) groups to control the activity of siRNA molecules. Caging groups have been applied to the backbone phosphates in both random (Shah et al., *Angew. Chem. Int. Ed.* 44:1328, 2005) and targeted approaches (Shah and Friedman, *Oligonucleolides* 17:35, 2007; Nguyen et al., *Biochim. Biophys. Acta* 1758:394, 2006). The problem with random caging was that either the inactivation or the activation was not complete (that is, fully inactive siRNA could not be entirely activated and vice versa). The targeted approach provided fully active siRNAs after irradiation, but suffered from substantial residual activity of the caged precursor. Others have caged an exocyclic base moiety at specific RNA bases to control siRNA, and noted instability on storage as a problem (Mikat and Heckel, *RNA* 13:2341, 2007).

Natural and unnatural nucleobase 'antisense' nucleobase polymers can interfere with specific gene expression when they are complementary to the target gene's 'sense' mRNA (Wagner, *Nature* 372:333, 1994; Crooke, *Annu. Rev. Med.* 55:61, 2004; *Antisense Drug Technology: Principles, Strategies, and Applications.* Second Edition. Edited by Stanley T. Crooke. CRC Press and Taylor & Francis Group, New York. 2007). Such antisense nucleobase polymers can reduce the stability and/or expression of the target mRNA by a variety of mechanisms including RNase H-mediated selective mRNA degradation, interference, and steric blockade of ribosomal machinery.

Therefore, there is a need in the art to the provide caged, non-stem loop RNA 1 duplex molecules having a photocleavable base moiety to effect light activated inhibition of gene expression. The present disclosure was made to address this need.

SUMMARY

The present disclosure provides a photocleavable sense-antisense nucleobase polymer complex comprising an unnatural antisense nucleobase polymer, and a photocleavable sense nucleobase polymer noncovalently bound to the antisense nucleobase polymer, wherein the photocleavable sense nucleobase polymer comprises a plurality of nucleobase polymers connected by a photocleavable linkage moiety. Preferably, the unnatural antisense nucleobase targets a specific mRNA sequence. Most preferably, the unnatural antisense nucleobase polymer is selected from the group consisting of morpholino, PNA, ncPNA, LNA, PS-DNA, PS-RNA, 2'-OMe-RNA and 2'-OMe-DNA. Preferably, the plurality of nucleobase polymers is selected from the group consisting of RNA, DNA, morpholino, PNA, ncPNA, LNA, PS-DNA, PS-RNA, 2'-OMe-RNA and 2'-OMe-DNA. Preferably, the photocleavable linkage comprises a nitro group attached to an aromatic group. Most preferably, the photocleavable linkage comprises a coumarin group. Preferably, the photocleavable sense nucleobase polymer further comprises a second photocleavable linkage. Preferably, the photocleavable sense-antisense nucleobase polymer complex further comprises a label. Most preferably, the label is selected from the group consisting of quantum dots, hydrophobic fluorophores, coumarin, rhodamine, fluorescein, radionucleotides, enzymes, substrates, cofactors, inhibitors, fluorescent moieties, chemiluminescent moieties, magnetic particles, donor/acceptor and fluorophore/quencher combinations, fluorescence resonance energy transfer (FRET)-based quenching, non-FRET based quenching, or wavelength-shifting harvester molecules terbium chelate and TRITC (tetrarhodamine isothiocyanate), lanthanide (e.g., europium or terbium) chelates and allophycocyanin (APC) or Cy5, europium cryptate and allophycocyanin, fluorescein and tetramethylrhodamine, IAEDANS and fluorescein, EDANS and DABCYL, fluorescein and DABCYL, fluorescein and fluorescein, BODIPY FL and BODIPY FL, fluorescein and QSY 7 dye, nonfluorescent acceptors, DABCYL and QSY 7 and QSY 33 dyes, and combinations thereof.

The present disclosure further provides a photocleavable sense-antisense nucleobase polymer complex comprising:

(a) an unnatural antisense nucleobase polymer that targets an mRNA; and (b) a photocleavable sense nucleobase polymer noncovalently bound to the antisense nucleobase polymer, wherein the photocleavable sense nucleobase polymer comprises a plurality of nucleobase polymers connected by a photocleavable linkage, The disclosure further provides a method for controlling time and spatial position of gene expression within a functioning multi-cellular organism, comprising:

(a) selecting a target mRNA sequence from a genome of the multi-cellular organism;

(b) introducing a photocleavable sense-antisense nucleobase polymer complex into a cell within the multi-cellular organism, wherein the photocleavable sense-antisense nucleobase polymer complex comprises an unnatural antisense nucleobase polymer that targets the mRNA target sequence; and a photocleavable sense nucleobase polymer noncovalently bound to the antisense nucleobase polymer, wherein the photocleavable sense nucleobase polymer comprises a plurality of nucleobase polymers connected by a photocleavable linkage; and (c) selectively irradiating the cell with light.

DETAILED DESCRIPTION

The present disclosure provides a photocleavable sense-antisense nucleobase polymer complex capable of modulating gene expression. More specifically, the photocleavable sense-antisense nucleobase polymer complex comprises:

(a) an unnatural antisense nucleobase polymer that targets an mRNA; and (b) a photocleavable sense nucleobase polymer noncovalently bound to the antisense nucleobase polymer, wherein the photocleavable sense nucleobase polymer comprises a plurality of nucleobase polymers connected by a photocleavable linkage. In one embodiment shown in FIG. 1, the photocleavable sense nucleobase polymer is formed from two nucleobase polymers connected by a single centrally located photocleavable linkage.

The disclosure further provides a method for controlling time and spatial position of gene expression within a functioning multi-cellular organism, comprising:

(a) selecting a target mRNA sequence from a genome of the multi-cellular organism;

(b) introducing a photocleavable sense-antisense nucleobase polymer complex into a cell within the multi-cellular organism, wherein the photocleavable sense-antisense nucleobase polymer complex comprises an unnatural antisense nucleobase polymer that targets the mRNA target sequence; and a photocleavable sense nucleobase polymer noncovalently bound to the antisense nucleobase polymer, wherein the photocleavable sense nucleobase polymer comprises a plurality of nucleobase polymers connected by a photocleavable linkage; and (c) selectively irradiating the cell with light.

Surprisingly, the photocleavable sense-antisense nucleobase polymer complex is highly effective in modulating gene expression within cells, both spatially and temporally, using targeted light irradiation. Thus, a method is also disclosed for controlling the time and spatial position of gene expression comprising selecting a target mRNA, introducing the photocleavable sense-antisense nucleobase polymer complex into a cell, and selectively irradiating the cell with light.

Covalent attachment of sense and antisense strands in a hairpin configuration, as disclosed in the art, is unnecessary to achieve spatio-temporal control of gene expression with light using antisense nucleobase polymers. One advantage provided by the disclosed photocleavable sense-antisense complex is that no specialized chemical synthesis skill is required. Instead, the complex is assembled by end-users, such as molecular biologists, who typically lack such specialized skills, by a simple one-step mixing of components.

Figure 1:
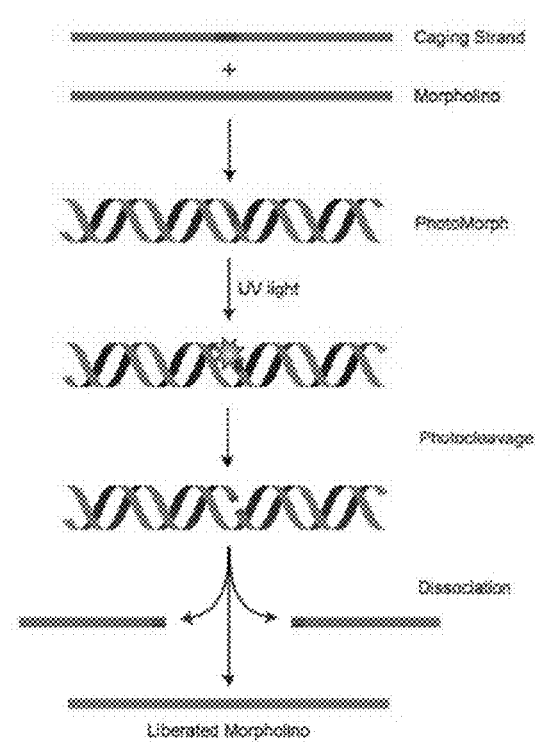
FIG. 1 is a schematic illustrating mRNA suppression by a photocleavable sense-antisense complex. The photocleavable sense nucleobase polymer is formed from two nucleobase polymers connected by a single centrally located photocleavable linkage.

Without being bound by theory, the intracellular mechanism of the disclosed photocleavable sense-antisense complex is as illustrated for the embodiment in FIG. 1. That is, the photocleavable sense nucleobase polymer prevents the antisense nucleobase polymer from binding its target mRNA. Upon light irradiation, the centrally-placed photocleavable linkage moiety cleaves and bisects the sense nucleobase polymer into two halves. It is believed that the binding stability of the two halves is significantly reduced relative to that of the intact sense nucleobase polymer. Thus, the two halves dissociate and release the antisense nucleobase polymer. The released antisense nucleobase polymer is then able to freely bind its target mRNA impacting cellular protein synthesis.

A. Definitions of Terminology

An "antisense" nucleobase polymer comprises a nucleobase sequence complementary to that of a target mRNA.

Two nucleobase polymers are said to "bind," if they associate noncovalently, such that a complex is formed. The ability to bind may be evaluated, for example, by determining a binding constant for the formation of the complex. The binding constant is the value obtained when the concentration of the complex is divided by the product of the component concentrations. In general, two nucleobase polymers are said to "bind," when a binding constant for complex formation exceeds about $10^3$ L/mol. A first nucleobase polymer is said to "specifically bind" relative to a second unrelated nucleobase polymer if the ratio of the first nucleobase polymer's binding constant to the second nucleobase polymer's binding constant is greater than 2, and preferably greater than 5.

The term "complementary" refers to electronic topologic compatibility or matching together of interacting surfaces of a nucleobase polymer with another nucleobase polymer, resulting in detectable binding using an appropriate assay technique. Thus, two nucleobase polymers that bind one another can be described as complementary, as can their contact surfaces. Depending on the degree of complementarily of two nucleobase polymers for a particular target nucleobase polymer as exhibited by their binding constants, one nucleobase polymer may be said to more specifically bind the target relative to the other (see "bind" above). In preferred embodiments, two nucleobase polymers are said to be "complementary" if the polymers are able to bind one another through base-pairing of their nucleobases (as in Watson-Crick base-pairing).

The term "exactly complementary" indicates that 100% of the nucleobases in a particular nucleobase polymer are able to engage in base-pairing with another nucleobase polymer. The term "substantially complementary" indicates that at least about 80% of the nucleobases in a particular nucleobase polymer are able to engage in base-pairing with another nucleobase polymer. The term "partially complementary" indicates that at least about 60% of the bases in a particular nucleobase polymer are able to engage in base-pairing with another nucleobase polymer.

"Expression" of a nucleic acid means transcription of DNA into RNA (optionally including modification of the RNA, e.g., splicing) and/or translation of encoded RNA (e.g., mRNA) into a polypeptide (possibly including subsequent modification of the polypeptide, e.g., post-translational modification), as indicated by the context.

"Hybridization" refers to binding of one nucleobase polymer to another nucleobase polymer via complementary regions. The polymers may be, for example, DNA, PNA, morpholino-based nucleobase polymers and/or other nucleobase polymers. Such base-pairing or aggregation should be detectable using standard assays (e.g., the detection of a marker linked to one nucleobase polymer). Whether or not a particular nucleobase polymer remains base-paired or aggregated with a target nucleobase polymer depends on the degree of complementarity, the length of the aggregated elements, and the stringency of the binding conditions. At a higher stringency, hybridization requires a higher degree of complementarity or length.

A "nucleobase polymer" is a polymer of nucleobases linked to a backbone. Both the nucleobases and the backbone may be naturally-occurring or non-naturally-occurring, or mixtures thereof.

A "sense" nucleobase polymer comprises a nucleobase sequence corresponding to that of a target mRNA.

"Stringency" refers to the combination of conditions that promote dissociation of complexes of aggregated nucleobase polymers (e.g., RNA:DNA; morpholino:DNA; morpholino:RNA; PNA:DNA, etc.). Common conditions that influence stringency include pH, temperature, and salt concentration.

A "target mRNA" is an mRNA whose expression is to be affected. A target mRNA can be, for example, a constitutively expressed mRNA or an inducible mRNA.

B. Antisense Nucleobase Polymer

An antisense nucleobase polymer is a nucleobase polymer that is at least partially complementary to a target mRNA, and which detectably modulates the expression and/or activity of the mRNA. The ability to modulate mRNA activity by antisense regulation is known in the art (reviewed in Uhlmann and Peyman, *Chem. Rev.* 90(4):544, 1990; Schreier, *Pharm. Acta Helv.* 68(3):145, 1994; Wagner, *Nature* 372:333, 1994; Crooke, *Annu. Rev. Med.* 55:61, 2004; *Antisense Drug Technology: Principles, Strategies, and Applications.* Second Edition. Edited by Stanley T. Crooke. CRC Press and Taylor & Francis Group, New York. 2007).

With respect to the modulation of gene expression, antisense molecules can be used not only to inhibit (i.e. attenuate) expression, but also to activate it in vitro and in vivo. Indirect activation of gene expression is accomplished, for example, by suppressing the biosynthesis of a natural repressor, as described for antisense oligodeoxynucleotides by Inoue (*Gene* 72:25, 1988). Direct activation of gene expression can be accomplished, for example, by reducing termination of transcription as described for antisense oligodeoxynucleotides by Winkler et al. (*Proc. Natl. Acad. Sci. USA* 79:2181, 1982). In embodiments where expression is attenuated, the antisense nucleobase polymer attenuates expression by at least about 10%, at least about 25%, at least about 50%, and preferably by at least about 75% or more, and most preferably to an undetectable level.

There are several in vitro and in vivo test systems known in the art that have been routinely used for assessing antisense activity (Crooke, *Anticancer Drug Des.* 6:609, 1991; Hanvey et al., *Science* 258:1481, 1992; Lisziewicz et al., *Proc. Natl. Acad. Sci. USA* 89.11209, 1992; Woolf et al., *Proc. Natl. Acad. Sci. USA* 89:7305, 1992; Nielsen et al., *Anticancer Drug Des.* 8:53, 1993 and Zeiphati et al., *Antisense Res. Dev.* 3:323, 1993).

A nucleobase is a nitrogenous heterocyclic group typically found in nucleic acids (such as the purine bases adenine and guanine, or the pyrimidine bases cytosine, thymine and uracil), or an analog of such a group capable of mediating binding between complementary nucleobase polymers. Nucleobases suitable for use in embodiments of antisense nucleobase polymers include the naturally-occurring nucleobases adenine, guanine, cytosine, thymine, uracil and the non-naturally-occurring analogs thereof, including, for example, purine bases in which the ring substituents are other than those found in adenine or guanine, or pyrimidine bases in which the ring substituents are other than those found in uracil, thymine and cytosine. A number of analogs of nucleobases are well known in the art; many of which have been tested as chemotherapeutic agents.

In some embodiments, it may be desirable to incorporate a nucleobase that binds non-specifically at a particular position. The nucleobase present in inosine is an example of such a non-specific binding analog. This can be used to incorporate degeneracy into antisense nucleobase polymers at particular positions which might be particularly useful, for example, in targeting a closely related family of target mRNAs that are homologous except for one or a few positions in their nucleobase sequences. Inosine can pair with all four natural nucleobases, although the strength of binding varies: dC>dA>dG/T. Alternatively, the universal nucleobase in 3-nitropyrrole-2'deoxynucleoside may be used to introduce degeneracy. In this strategy, the analog does not hybridize significantly to the other four natural nucleobases, but increases complex stability through stacking interactions.

Other types of modified nucleobases that may be of particular interest in certain embodiments are those which enhance binding affinity. For example, diaminopurine can form three hydrogen bonds with thymine, whereas adenine and thymine form only two. Similarly, pyridopyrimidine nucleobases can be used in place of cytosine to provide stronger pairing with guanine.

Nucleobases can also comprise any of a variety of "target receptor modifying groups". By way of illustration, nucleobases can function as cross-linking moieties. For example, 6-bromo-5,5-dimethoxyhexanohydrazide can be introduced into the $C^4$ position of cytidine to alkylate and thereby crosslink guanosine (Summerton and Bartlett, *J. Mol. Biol.* 122:145, 1978). $N^4,N^4$-Ethano-5-methyl-cytosine can be used to similar effect (Webb and Matteucci, *J. Am. Chem. Soc.* 108:2764, 1986; Cowart et al., *Biochemistry* 28:1975, 1989).

A wide range of purine and pyrimidine analogs exhibiting various properties is known in the art, and are suitable for use a nucleobases in various embodiments antisense nucleobase polymers (reviewed in Conholly, *Methods Enzymol.* 211:36, 1992; Lin and Brown, *Methods Mol. Biol.* 26:187, 1994 and Meyer, *Methods Mol. Biol.* 26:73, 1994). Such analogs include, for example, bromothymine, azaadenines and azaguanines. An exemplary but not exhaustive list of such analogs includes: 1-methyladenine, 1-methylguanine, 1-methylinosine, 1-methylpseudouracil, 2-methylthio-$N^6$-isopentenyladenine, 2-thiocytosine, 2-methyladenine, 2-methylguanine, 2-thiouracil, 2,2-dimethylguanine, 2,6-diaminopurine-3-methylcytosine, 3-(3-amino-3-$N^2$-carboxypropyl)-uracil-4-acetylcytosine, 4-thiouracil, 5-fluorouracil, 5-iodouracil, 5-bromouracil, 5-methyluracil, 5-methyl-2-thiouracil, 5-methoxyaminomethyl-2-thiouracil, 5-chlorouracil, 5-carboxymethylaminomethyl-2-thiouracil, 5-methylaminomethyluracil, 5-carboxyhydroxylmethyluracil, 5-carboxymethylaminomethyluracil, 5-methoxyuracil, 5-methylcytosine, 7-methylguanine, 7-deazaguanine, 7-deazaadenine, beta-D-mannoseylqueosine, beta-D-galactosylqueosine, dihydrouracil, hypoxanthine, inosine, N-uracil-5-oxyacetic acid methylester, $N^6$-methyladenine, $N^6$-isopentenyladenine, pseudouracil, queosine, uracil-5-oxyacetic acid methylester, uracil-5-oxyacetic acid and xanthine. Preferred naturally-occurring and non-naturally-occurring nucleobases are those commercially provided as phosphoramidite monomers by Glen Research, Inc. (Glen Research, Sterling, Va.). See for example, *Beilstein's Handbuch der Organischen Chemie* (Springer Verlag, Berlin), and Chemical Abstracts, which provide references to publications describing the properties and preparation of such nucleobases.

The backbone in embodiments of antisense nucleobases polymers may also be naturally-occurring (as in a nucleic acid molecule) or may be non-naturally-occurring. Nucleobase polymers with non-naturally-occurring backbones are preferably resistant to degradative enzymes within the cell (e.g., nucleases). Thus, an antisense nucleobase polymer comprises a polymer of nucleobases linked to a backbone Representative examples of nucleobase polymers suitable for use as the antisense nucleobase polymer include peptide nucleic acids or 'PNA' (Buchardt et al., PCT WO 92/20702 and Buchardt et al., U.S. Pat. No. 5,719,262, the disclosures of which are incorporated by reference herein), negatively-charged PNA or 'ncPNA' (Efimov et al., *Nucleosides Nucleotides Nucleic Acids* 20(4-7):419, 2001; Wickstrom et al., *Methods Cell Biol.* 77:137, 2004; Urtishak et al., *DeV. Dyn.* 228:405, 2003), morpholino-based nucleobase polymers or 'morpholinos' (Summerton and Weller, U.S. Pat. No. 5,698,685; Summerton et al., U.S. Pat. No. 5,378,841 and Summerton and Weller, U.S. Pat. No. 5,185,444, the disclosures of which are incorporated by reference herein), peptide-base nucleic acid mimics or 'PENAMs' (U.S. Pat. No. 5,698,685 the disclosure of which is incorporated by reference herein), locked-nucleic acid or 'LNA' (Vester and Wengel, *Biochemistry* 43(42):13233, 2004), PS-DNA or PS-RNA (PS is phosphorothioate), and polynucleosides with linkages comprising carbamate (Stirchak and Summerton, *J. Org. Chem.* 52:4202, 1987), amide (Lebreton et al., *Synlett.* February 1994:137), methylhydroxylamine (Vasseur et al., *J. Am. Chem. Soc.* 114: 4006, 1992), 3'-thioformacetal (Jones et al., *J. Org. Chem.* 58:2983, 1993), sulfamate (U.S. Pat. No. 5,470,967 the disclosure of which is incorporated by reference herein) and others as disclosed in Swaminathan et al., U.S. Pat. No. 5,817,781 (the disclosure of which is incorporated by reference herein) and Freier and Altmann, *Nucl. Acids Res.* 25:4429, 1997, and references cited therein. Hybrids, chimeras and mixtures of any of the above are also possible embodiments.

Preferred nucleobase polymers suitable for use as the antisense nucleobase polymer include morpholinos, PNA, ncPNA, LNA, PS-DNA, PS-RNA, 2'-OMe-DNA and 2'-OMe-RNA. Morpholinos are particularly preferable as the antisense nucleobase polymer for use in zebrafish.

The number (N) of nucleobases in an antisense nucleobase polymer is in principle, without limit, potentially exceeding the number of bases in the target mRNA. However, practical limits on synthesis make the preferred N less than 50, and even more preferably the N is less than 30 but greater than 18.

C. Photocleavable Sense Nucleobase Polymer

The nucleobases and the backbone of the photocleavable sense nucleobase polymer comprise any of those elements described above for the antisense nucleobase polymer. DNA is less preferred as the sense nucleobase polymer however due to greater toxicity at higher concentrations, presumably due to the p53 DNA damage pathway. The distinguishing feature of the photocleavable sense nucleobase polymer is the presence of one or a plurality of photocleavable linkages that on irradiation cause the sense nucleobase polymer to cleave into a plurality of shorter nucleobase polymers. In preferred embodiments, the one or more photolabile linkages are cleaved by exposure to light with a wavelength between about 60 nm and about 400 nm, between about 400 nm and about 700 nm, and more preferably between about 320 nm and about 420 nm.

Photolabile moieties suitable for use in embodiments of the photocleavable sense nucleobase polymer include those previously described and reviewed (Pellicciolo and Wirz, *Photochem. Photobiol. Sci.* 1:441, 2002; Goeldner and Givens, *Dynamic Studies in Biology*, Wiley-VCH, Weinheim, 2005; Marriott, *Methods in Enzymology*, Vol. 291, Academic Press, San Diego, 1998; Morrison, *Bioorganic Photochemistry*, Vol. 2, Wiley, New York, 1993; Adams and Tsien, *Annu. Rev.*

Physiol. 55:755, 1993; Mayer and Heckel, *Angew. Chem. Int. Ed.* 45:4900, 2006; Pettit et al., *Neuron* 19:465, 1997; Furuta et al., *Proc. Natl. Acad. Sci. USA* 96:1193, 1999; and U.S. Pat. Nos. 5,430,175; 5,635,608; 5,872,243; 5,888,829; 6,043,065, the disclosures of which are incorporated by reference herein).

For example, the ortho-nitro aromatic core scaffold can been adapted using routine chemical syntheses to serve as the photolabile linkage in a wide variety of embodiments including those that comprise ortho-nitro benzyl (ONB), 1-(2-nitrophenyl)ethyl (NPE), alpha-carboxy-2-nitrobenzyl (CNB), 4,5-dimethoxy-2-nitrobenzyl (DMNB), 1-(4,5-dimethoxy-2-nitrophenyl)ethyl (DMNPE), 5-carboxymethoxy-2-nitrobenzyl (CMNB) and ((5-carboxymethoxy-2-nitrobenzyl)oxy)carbonyl (CMNCBZ) photolabile cores. The substituents on the aromatic core are selected to tailor the wavelength of absorption, with electron donating groups (e.g., methoxy) generally leading to longer wavelength absorption.

Other ortho-nitro aromatic core scaffolds include those that trap nitroso byproducts in a hetero Diels Alder reaction (Pirrung et al., *J. Org. Chem.* 68:1138, 2003). The nitrodibenzofurane chromophore offers an extinction coefficient significantly higher in the near UV region, which is commonly used for uncaging, but it also has a very high quantum yield for the deprotection reaction and it is suitable for two-photon activation (Momotake et al., *Nat. Methods* 3:35, 2006). The NPP group is an alternative introduced by Pfleiderer et al. that yields a less harmful nitrostyryl species (Walbert et al., *Helv. Chim. Acta* 84:1601, 2001).

Preferred photolabile linkages (arrows indicate broken bonds after irradiation) suitable for use in embodiments of the photocleavable sense nucleobase polymer include linkage 1 (Ordoukhanian and Taylor, *J. Am. Chem. Soc.* 117:9570, 1995; Ordoukhanian and Taylor, *Bioconjugate Chem.* 11:94, 2000), linkage 2 (Zhang and Taylor, *J. Am. Chem. Soc.* 121:11579, 1999), linkage 3 (Zhang and Taylor, *Biochemistry* 40:153, 2001), linkage 4 (Dussy et al., *ChemBioChem* 3:54, 2002), and linkage 5 (Glen Research, Sterling, Va.).

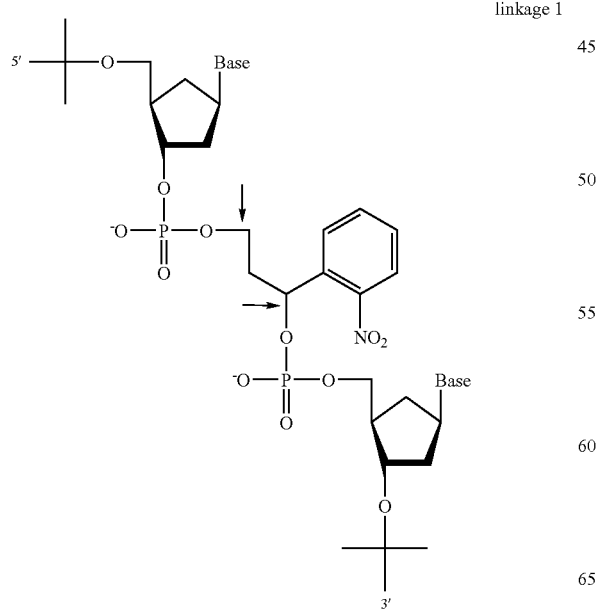

linkage 1

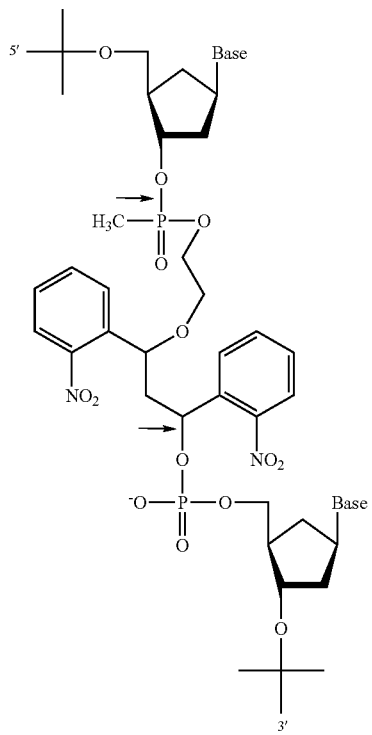

linkage 2

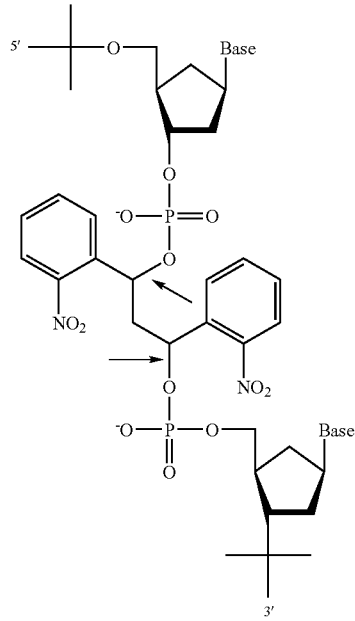

linkage 3

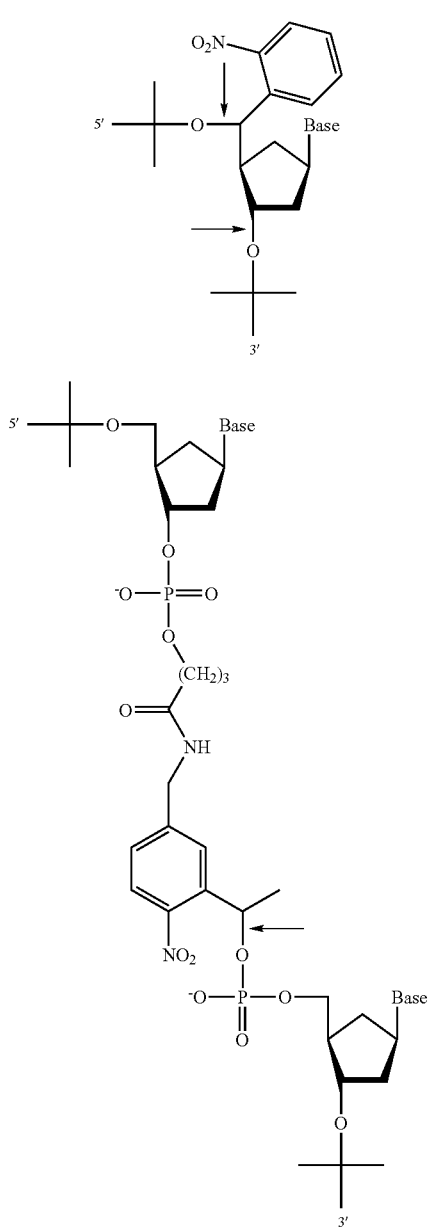

Other suitable photolabile linkages are based on the coumarin system, such as Bhc (Furuta and Iwamura, *Methods Enzymol.* 291:50, 1998; Furuta et al., *Proc. Natl. Acad. Sci. USA* 96:1193, 1999; Suzuki et al., *Org. Lett.* 5:4867, 2003; U.S. Pat. No. 6,472,541, the disclosure of which is incorporated by reference herein). The DMACM linkage photocleaves in nanoseconds (Hagen et al., *ChemBioChem* 4:434, 2003) and is cleaved by visible light (U.S. patent application Ser. No. 11/402,715 the disclosure of which is incorporated by reference herein). Coumarin-based photolabile linkages are also available for linking to aldehydes and ketones (Lu et al., Dore, *Org. Lett.* 5:2119, 2003). Closely related analogues, such as BHQ, are also suitable (Fedoryak and Dore, *Org. Lett.* 4:3419, 2002).

Another suitable photolabile linkage comprises the pHP group (Park and Givens, *J. Am. Chem. Soc.* 119:2453, Givens et al., *J. Am. Chem. Soc.* 122:2687, 2000; 1997; Zhang et al., *J. Am. Chem. Soc.* 121:5625, 1999; Conrad II et al., *J. Am. Chem. Soc.* 122:9346, 2000; Conrad II et al., *Org. Lett.* 2:1545, 2000). A ketoprofen derived photolabile linkage is also suitable (Lukeman and Scaiano, *J. Am. Chem. Soc.* 127:7698, 2005).

D. Labels

The nucleobase polymers optionally include one or more labels. In certain embodiments, labels are useful for detecting the location of a photocleavable sense-antisense complex, extent of binding between the antisense and sense nucleobase polymers to one another (e.g., when each member of a FRET pair is coupled to each polymer in a complex), or the extent of its photocleavage (e.g., a FRET pair coupled to the photocleavable sense nucleobase polymer termini results in increased fluorescence signal after cleavage by irradiation since each cleaved half separates from one another).

A label is a moiety that facilitates detection of a molecule. Common labels, in the context of this disclosure, include fluorescent, luminescent, and/or colorimetric labels. Suitable labels more generally include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241, the disclosures of which are incorporated by reference herein. Many labels are commercially available.

A number of fluorescent labels are well known in the art, including but not limited to, quantum dots, hydrophobic fluorophores such as coumarin, rhodamine and fluorescein (see Haughland (2002) *Handbook of Fluorescent Probes and Research Products*, Ninth Edition or the current Web Edition, available now from Invitrogen, Inc.).

Likewise, a variety of donor/acceptor and fluorophore/quencher combinations, using fluorescence resonance energy transfer (FRET)-based quenching, non-FRET based quenching, or wavelength-shifting harvester molecules, are known. Example combinations include terbium chelate and TRITC (tetrarhodamine isothiocyanate), lanthanide (e.g., europium or terbium) chelates and allophycocyanin (APC) or Cy5, europium cryptate and Allophycocyanin, fluorescein and tetramethylrhodamine, IAEDANS and fluorescein, EDANS and DABCYL, fluorescein and DABCYL, fluorescein and fluorescein, BODIPY FL and BODIPY FL, and fluorescein and QSY 7 dye. Nonfluorescent acceptors such as DABCYL and QSY 7 and QSY 33 dyes have the particular advantage of eliminating background fluorescence resulting from direct (i.e., nonsensitized) acceptor excitation. See, U.S. Pat. Nos. 5,668,648, 5,707,804, 5,728,528, 5,853,992, and 5,869,255, the disclosures of which are incorporated by reference herein for a description of FRET dyes. The label and quencher can be attached to a nucleobase polymer of the disclosure at essentially any suitable position(s), e.g., at the 3' end, at the 5' end, and/or within either or both the sense and antisense nucleobase polymers.

For use of quantum dots as labels for biomolecules, see Dubertret et al. *Science* 298:1759, 2002; *Nature Biotechnology* 21:41, 2003; and *Nature Biotechnology* 21:47, 2003.

Other optically detectable labels are used. For example, gold beads are used as labels and are detected using a white light source via resonance light scattering. See, http://www-.geniconsciences.com. Suitable non-optically detectable labels are also known in the art. For example, magnetic labels are used (e.g., 3 nm superparamagnetic colloidal iron oxide as a label and NMR detection; see *Nature Biotechnology* 20:816-820, 2002).

Labels are introduced to antisense and sense nucleobase polymers during synthesis or by postsynthetic reactions by techniques established in the art. For example, a fluorescent phosphoramidite is incorporated during phosphoramidite triester synthesis of the nucleobase polymer at a preselected position. Alternatively, fluorescent labels are added by postsynthetic-reactions, at either random or preselected positions (e.g., a nucleobase polymer is chemically synthesized with a terminal amine or free thiol at a preselected position, and a fluorophore is coupled to the nucleobase polymer via reaction with the amine or thiol). Reagents for fluorescent labeling of nucleobase polymers are commercially available (e.g., Glen Research, Inc., Sterling, Va.). Quenchers are introduced by analogous techniques.

Attachment of labels to nucleobase polymers during automated synthesis and by post-synthetic reactions has been described (Tyagi and Kramer, *Nature Biotechnology* 14:303, 1996; and U.S. Pat. Nos. 6,037,130 and 5,925,517, the disclosures of which are incorporated by reference herein). Additional details on synthesis of functionalized nucleobase polymers is found in Nelson, et al., *Nucleic Acids Res.* 17:7187, 1989.

Labels and/or quenchers are introduced to the nucleobase polymers, for example, by using a controlled-pore glass column to introduce a quencher (such as, 4-dimethylaminoazobenzene-4'-sulfonyl moiety (DABSYL)). For example, the quencher is added at the 3' (or equivalent for a particular nucleobase polymer chemistry) end of nucleobase polymers during automated synthesis; a succinimidyl ester of 4-(4'-dimethylaminophenylazo)benzoic acid (DABCYL) is used when the site of attachment is a primary amino group; and 4-dimethylaminophenylazo-phenyl-4'-maleimide (DABMI) is used when the site of attachment is a sulphydryl group.

Similarly, fluorescein is introduced into nucleobase polymers assembled by phosphoramidite chemistry, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein is coupled to a sulphydryl group. Tetrachlorofluorescein (TET) is introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. Labeled oligonucleotides are purified, if desired, such as by high pressure liquid chromatography (hplc) or other methods.

Similarly, signals from the labels (e.g., absorption by and/or fluorescent emission from a fluorescent label) are detected by essentially any method known in the art. For example, multicolor detection, detection of FRET, including, time-resolved or TR-FRET between lanthanide chelate donors and fluorescent dye acceptors (see, *Journal of Bimolecular Screening* 7:3, 2002), and the like, are known in the art. In brief, FRET (Fluorescence Resonance Energy Transfer) is a non-radiative energy transfer phenomenon in which two fluorophores with overlapping emission and excitation spectra, when in sufficiently close proximity, experience energy transfer by a resonance dipole induced dipole interaction. The phenomenon is commonly used to study the binding of analytes such as nucleic acids, proteins and the like. FRET is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (see Haughland (2002) *Handbook of Fluorescent Probes and Research Products*, Ninth Edition or the current Web Edition, available now from Invitrogen, Inc.).

As another example, fluorescence polarization is used. Briefly, in the performance of such fluorescent polarization assays, a typically small, fluorescently labeled molecule, e.g., a ligand, antigen, etc., having a relatively fast rotational correlation time, is used to bind to a much larger molecule, e.g., a receptor protein, antibody etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule. Generally, fluorescence polarization level is calculated using the following formula: $P=[I_1-I_2]/[I_1+I_2]$, where $I_1$ is the fluorescence detected in the plane parallel to the excitation light, and $I_2$ is the fluorescence detected in the plane perpendicular to the excitation light. Several references discuss fluorescence polarization and/or its use in molecular biology (Perrin, *J. Phys. Radium* 7:390, 1926; Weber, *Adv. Protein Chem.* 8:415, 1953; Weber, *J. Opt. Soc. Ant.* 46:962, 1956; Dandliker and Feigen, *Biochem. Biophys. Res. Commun.* 5:299, 1961; Dandliker and de Saussure, 7:799, 1970; Dandliker et al., *Immunochemistry* 10:219, 1973; Levison et al., *Endocrinology* 99:1129, 1976; Jiskoot et al., *Anal. Biochem.* 196:421, 1991; Wei and Herron, *Anal. Chem.* 65:3372, 1993; Devlin et al., *Clin. Chem.* 39:1939, 1993; Murakami et al., *Nucleic Acids Res.* 19:4097, 1991; Checovich et al., *Nature* 375:354, 1995; Kumke et al., *Anal. Chem.* 67:21, 3945, 1995; Walker et al., *Clin. Chem.* 42(1):9, 1996).

Techniques for determining and verifying suitable positions for a label and/or quencher are known. For example, the label and quencher are typically positioned such that they do not substantially reduce modulation of the target mRNA as compared to an otherwise identical photolabile sense-antisense complex lacking the label and quencher (e.g., the label and quencher preferably do not interfere with binding of the antisense nucleobase polymer to the target mRNA).

E. Synthesis Methods

Methods of chemical synthesis of the antisense nucleobase polymer and the photocleavable sense nucleobase polymer are found in the corresponding references cited above. A preferred chemical synthesis strategy is by coupling commercially available phosphoramidites using commercially available automated synthesizers.

In general, synthetic methods for making oligonucleotides, morpholinos, PNA, ncPNA, LNA, PS-DNA, PS-RNA, 2'-OMe-DNA and 2'-OMe-RNA are known (including labeled versions thereof). For example, oligonucleotides can be synthesized chemically according to the solid-phase phosphoramidite triester method (Beaucage and Caruthers, *Tetrahedron Lett.* 22(20):1859, 1981), using a commercially available automated synthesizer (Needham-VanDevanter et al., *Nucleic Acids Res.* 12:6159, 1984). Synthesis of PNAs and modified nucleobase polymers (e.g., oligonucleotides comprising 2'-O-methyl nucleotides and/or phosphorothioate, methylphosphonate, or boranophosphate linkages) are described in *Oligonucleotides and Analogs* (1991), IRL Press, New York; Shaw et al., *Methods Mol. Biol.* 20:225, 1993; Nielsen et al., *Science* 254:1497, 1991; and Shaw et al., *Methods Enzymol.* 313:226, 2000.

Natural and unnatural nucleobase polymers (e.g., PNA, ncPNA, LNA, 2'-O-methyl nucleotides, phosphorothioate, methylphosphonate, or boranophosphate linkages), including those comprising labels (e.g., fluorophores and quenchers), can be ordered from a variety of commercial sources. There are many commercial providers of nucleobase polymer synthesis services. Examples of commercial sources include Integrated DNA Technologies (www.idtdna.com), The Midland Certified Reagent Company (www.mcrc.com), Trilink Biotechnologies, Inc. (www.trilinkbiotech.com), The Great American Gene Company (www.genco.com), ExpressGen Inc. (www.expressgen.com), QIAGEN (http://oligos.qiagen.com), Dharmacon (www.dharmacon.com), and others.

F. Photocleavable Sense-Antisense Complex

One class of embodiments provides a composition comprising a photocleavable sense-antisense complex. In a preferred embodiment, the photocleavable sense-antisense complex comprises an unnatural antisense nucleobase polymer directed to a target mRNA, and a photocleavable sense nucleobase polymer noncovalently bound to the antisense nucleobase polymer, wherein the photocleavable sense nucleobase polymer comprises a plurality of nucleobase polymers connected by a photocleavable linkage.

The photolabile sense nucleobase polymer inhibits (prevents) the antisense nucleobase polymer from binding its target mRNA in a cell comprising the photocleavable sense-antisense complex. The photolabile sense nucleobase polymer alter the antisense nucleobase polymer modulating ability (i.e. ability to modulate expression of the target mRNA) by at least about 25%, at least about 30%, at least about 35%, at least about 50%, at least about 75%, and more preferably at least about 90%, as compared to the antisense nucleobase polymer in the absence of the photolabile sense nucleobase polymer.

The antisense nucleobase polymer is at least partially complementary to the target mRNA. The photocleavable sense-antisense complex has at least one double-stranded region, the double-stranded region comprising the region of noncovalent binding between the photocleavable sense nucleobase polymer and the antisense nucleobase polymer. The double-stranded region in the antisense nucleobase polymer is at least partially complementary, and more preferably substantially complementary to the corresponding region in the photocleavable sense nucleobase polymer. In embodiments where the two nucleobase polymers are exactly complementary to one another, the photolabile linkage loops out from the complex to accommodate base-pairing of all nucleobases.

The photocleavable sense-antisense complex has a variety of structures, lengths, and compositions. Thus, in one class of embodiments, the complex is a long double-stranded complex, or it is relatively short. It may have completely flush ends, or the constituent nucleobase polymers has overhang extensions of any length that are uninvolved in the double-stranded region. Overhangs are used to reduce synthesis costs by using shorter polymers. Synthetic capabilities place practical limits on the lengths that synthetic nucleobase polymers assume (i.e., less than about 100 nucleobases). Thus, in preferred embodiments, each nucleobase polymer comprises between 15 and 50, and more preferably 20 and 30 nucleobases. The double-stranded region preferably involves at least 25%, at least 50%, at least 75%, and more preferably at least 90% of the bases in the antisense nucleobase polymer. Preferably, both ends are flush.

The photocleavable sense nucleobase polymer has a single photolabile linkage or a plurality of photolabile linkages. If a plurality of photolabile linkages is employed, they are connected nucleobase polymer segments of uniform or irregular length in linear order, either with one or a plurality (i.e., tandem photolabile linkages) of photolabile linkages interposed between the connected segments. For a double-stranded region of 30 nucleobases or less, there are no more than 5 photolabile linkages in the sense nucleobase polymer, with a single centrally located linkage being preferred.

Initially, it was presumed that the size occupied by the photolabile linkage would require eliminating a certain number of nucleobases from the sense nucleobase polymer relative to the nucleobase sequence in the complementary antisense nucleobase polymer (e.g., linkages 1-5 above are predicted to occupy a gap of 1 to 2 nucleobases). Surprisingly, this is not necessary and in some embodiments eliminating no nucleobases in the sense nucleobase polymer resulted in a complex that was more effectively inactivated than complexes made from a sense polymer with the predicted number of nucleobases eliminated. In general, the elimination of 0 to 2 nucleobases for each photolabile linkage is about equally tolerated. Thus, in preferred embodiments, a single centrally located photolabile linkage is placed in the photocleavable sense nucleobase polymer with no nucleobases eliminated relative to the complementary antisense nucleobase polymer.

Techniques for determining and verifying suitable positions for the photolabile linkage and the suitable number to install into the sense nucleobase polymer are known in the art. For example, the number and positions of photolabile linkages are selected such that they do not substantially reduce the ability of the sense nucleobase polymer to prevent modulation of the target mRNA by the antisense nucleobase polymer as compared to an otherwise identical sense nucleobase polymer lacking the photolabile linkages (e.g., the photolabile linkages preferably do not interfere with sense nucleobase polymer binding to antisense nucleobase polymer binding). In-cell techniques for testing the suitable number and positions of photolabile linkages are preferable, although in vitro methods are also acceptable (e.g., measuring melting temperature and other physicochemical measures of binding stability between the sense and antisense nucleobase polymers).

In preferred embodiments, the photocleavable sense-antisense complex is formed by mixing (i.e., annealing) the antisense nucleobase polymer with the photocleavable sense nucleobase polymer. In preferred embodiments, a brief heating of the nucleobase polymers to about 90° C., followed by slow cooling over about an hour, promotes complete formation of the complex. During complex formation and complex use within a cell, the ratio of sense to antisense nucleobase polymers is 1:1, 2:1, and more preferably greater than 5:1. Without being limited by theory, it is believed that higher ratios exceeding 5:1 are preferred based on Le Chatelier arguments that require an excess of the sense polymer in order to completely bind and render inactive the antisense nucleobase polymer.

The photocleavable sense-antisense complex is optionally nuclease resistant. A complex (or nucleobase polymer) that is "nuclease resistant" or "resistant to nuclease activity" is cleaved more slowly under typical reaction conditions for a given nuclease (e.g., a 5' to 3' nuclease and/or an endonuclease) than is a corresponding nucleic acid comprising only the four conventional deoxyribonucleotides (A, T, G, and/or C), or the four conventional ribonucleotides (U, A, G, and/or C), and phosphodiester linkages. For example, nucleobase polymers that incorporate 2' O methylated nucleotides are typically more nuclease resistant than nucleic acids that incorporate only conventional nucleotides.

The photocleavable sense-antisense complex optionally also includes at least one label, wherein irradiation induced cleavage of the sense nucleobase polymer in the cell results in a signal output of the label. In a preferred class of embodiments, the label is a fluorescent label, and the change in the signal output of the label is a change in fluorescent emission.

In another class of embodiments, the photocleavable sense-antisense complex includes at least one label and one quencher and the change in the signal output of the label is a change in fluorescent emission from the label. The label and the quencher are positioned in the complex such that fluorescent emission by the label is quenched by the quencher (which is itself a label whose absorption spectrum overlap the emission spectrum of the other label). Irradiation induced cleavage of the sense nucleobase polymer in the cell results in unquenching of the label, and thus an increase in the fluorescent emission by the label. Examples of suitable arrangements include the label and quencher positioned on opposite nucleobase polymers on the same or opposite ends, or both on the sense nucleobase polymer, which in both cases will the label and quencher separating from one another on irradiation.

In another class of embodiments, the sense polymer comprises a first label and the antisense polymer a second label. The two labels are different, non-interacting fluorophores with distinct emission spectra (e.g., red and green, such that the double-stranded sense-antisense complex is yellow while the single strands are red and green).

The composition optionally also includes the target mRNA and/or a cell, such as a zebrafish embryo pre-injected with the photocleavable sense-antisense complex. Various techniques (e.g., lipofection, microinjection, or electroporation) are used to introduce the photocleavable sense-antisense complex into a cell (see section below). In one class of embodiments, the photocleavable sense-antisense complex also includes a cellular delivery module, associated with the photocleavable sense-antisense complex, which mediates its introduction into the cell (see section below, e.g., cellular delivery modules comprising polypeptides, amphipathic peptides, protein transduction domains, and lipids).

G. In Vivo and In Vitro Cellular Delivery

The photocleavable sense-antisense complex is introduced into cells by traditional methods such as lipofection, electroporation, microinjection (preferred in zebrafish), optofection, laser transfection, calcium phosphate precipitation, and/or particle bombardment (see also WO03/040375, the disclosure of which is incorporated by reference herein). Reagents for delivery of the photocleavable sense-antisense complex are commercially available, e.g., TransIT-TKO™ (Mirus Corporation, www.genetransfer.com).

The photocleavable sense-antisense complex is optionally associated (covalently or non-covalently) with a cellular delivery module that mediates its introduction into the cell. The site of attachment of the cellular delivery module is anywhere, e.g. sense nucleobase polymer, antisense nucleobase polymer or the photolinkage itself.

The cellular delivery module is typically, but need not be, a polypeptide, for example, a PEP-1 peptide, an amphipathic peptide, e.g., an MPG peptide (Simeoni et al., *Nucleic Acids Res.* 31: 2717, 2003), a cationic peptide (e.g., a homopolymer of lysine, histidine, or D-arginine), or a protein transduction domain. A protein transduction domain is a polypeptide that mediates introduction of a covalently associated, molecule into a cell (Fischer et al., *Bioconjug Chem.*, 12:825; Gros et al., *Biochim. Biophys. Acta.* 1758(3):384, 2006; Murriel and Dowdy, *Expert Opin. Drug Deliv.* 3(6):739, 2006; Chauhan et al., *J. Control Release.* 117(2):148, 2007).

For example, the antisense nucleobase polymer (or alternatively the sense nucleobase polymer) portion of the complex is covalently associated with a protein transduction domain, such as an HIV TAT sequence, which most cells naturally uptake, the herpes simplex virus protein VP22, and the *Drosophila* protein antennapedia (Penetratin™), or a short D-arginine homopolymer (e.g., eight contiguous D-arginine residues). The protein transduction domain-coupled complex is added to cell culture or injected into an animal for delivery. In other embodiments, TAT and D-arginine homopolymers, alternatively, are noncovalently associated with the complex and still mediate its introduction into the cell.

The photocleavable sense-antisense complex is also introduced into cells by covalently or noncovalently attached lipids, e.g., by a covalently attached myristoyl group. In any of the cellular delivery modules used herein, lipids used for lipofection are optionally excluded from cellular delivery modules in some embodiments.

The cell into which a photocleavable sense-antisense complex is introduced is typically a eukaryotic cell (such as, a yeast, a vertebrate cell, a mammalian cell, a rodent cell, a primate cell, a human cell, a plant cell, an insect cell, or essentially any other type of eukaryotic cell). The cell is in culture or in a tissue, fluid, etc. and/or from or in an organism.

The amount of a photocleavable sense-antisense complex delivered to a cell is optionally controlled by controlling the number of cellular delivery modules associated with a photocleavable sense-antisense complex (covalently or noncovalently). For example, increasing the ratio of 8-D-Arg to a complex increases the percentage of complex that enters the cell.

The photocleavable sense-antisense complex optionally also comprises a subcellular delivery module (e.g., a peptide, nucleic acid, and/or carbohydrate tag) or other means of achieving a desired subcellular localization. Examples of subcellular delivery modules include nuclear localization signals, chloroplast stromal targeting sequences, and many others (see, e.g., *Molecular Biology of the Cell* (3rd ed.) Alberts et al., Garland Publishing, 1994; and *Molecular Cell Biology* (4th ed.) Lodish et al., W H Freeman & Co, 1999). Similarly, localization is to a target protein; that is, the subcellular delivery module comprises a binding domain that binds the target protein.

The covalent attachment between the protein transduction domain and the complex is itself optionally reversible by exposure to light of a preselected wavelength. Similarly, the protein transduction domain is attached to the complex through a disulfide bond or an ester linkage that is preferably reduced or cleaved by non-specific esterases once the complex is inside the cell.

Kits for making the protein transduction domain-linked complexes are also a feature in certain embodiments. For example, one embodiment provides a kit comprising a complex, a protein transduction domain, and instructions for assembling the RNA and the protein transduction domain to form the composition, packaged in one or more containers.

Embodiments are also provided that provides a related method for introducing a complex into a cell. Specifically there is disclosed a composition comprising a complex and a protein transduction domain covalently attached to the complex. The composition and the cell are contacted, whereby the protein transduction domain mediates introduction of the complex into the cell.

In another aspect, automated systems and/or apparatus comprising the compositions noted above and, components such as detectors, fluid handling apparatus, sources of light of a predetermined wavelength, or the like, are a feature in certain embodiments (see below).

Kits for making the lipid-linked RNAs are also a feature of certain embodiments. For example, one embodiment provides a kit comprising a complex, a lipid, and instructions for assembling the complex and the lipid to form the composition, packaged in one or more containers.

Other embodiments also provide methods of introducing into a cell a composition comprising a complex and a lipid covalently attached to the complex. The composition and the cell are contacted, whereby the lipid mediates introduction of the complex into the cell.

H. Spatiotemporal Cleavage Methods

This disclosure provides methods for selectively modulating (e.g., attenuating) expression of a target mRNA in a cell containing a photocleavable sense-antisense complex (the 'complex') using targeted light irradiation. In one embodiment, modulation of the target mRNA is initiated by exposing the cell containing a complex to light of a predetermined wavelength. Irradiation at the predetermined wavelength cleaves the photolabile sense nucleobase polymer, presumably freeing the antisense nucleobase polymer from the sense nucleobase polymer and thereby permitting the antisense nucleobase polymer to bind the target mRNA.

It is worth noting that modulation of the target mRNA by the photocleavable sense-antisense complex (the 'complex') can, but need not, result in a substantial attenuation of expression of the target mRNA. For example, expression of the target mRNA is decreased or increased (see section B. Antisense Nucleobase Polymer) by an antisense nucleobase polymer in the complex.

Appropriate methods for irradiating and cleaving the complex are known in the art. For example, appropriate wavelengths of light for cleaving the photolabile linkages in the sense nucleobase polymer have been described; e.g., 300-360 nm for 2-nitrobenzyl, 350 nm for benzoin esters, and 740 nm for brominated 7-hydroxycoumarin-4-ylmethyls (two-photon). Conditions for cleaving the photolabile sense nucleobase polymer in the complex (e.g., the optimal wavelength for cleavage) is determined according to methods known in the art. Instrumentation and devices for delivering a light of suitable energy and wavelength are likewise known. For example, well known and useful light sources include e.g., a lamp, a laser (e.g., a laser optically coupled to a fiber-optic delivery system) or a light-emitting compound.

The exposure to light can be addressable; e.g., the complex can be exposed to light comprising a predetermined wavelength by exposing one or more preselected areas (e.g., wells of a microtiter plate or portions thereof, or the like) to the light. As another example, the light can be directed at a preselected subset of a cell population comprising the cell, or a subset of cells within a whole organism (e.g. zebrafish, c. elegans, drosophila).

Exposing the cell to light comprising a predetermined wavelength optionally comprises exposing the cell to light such that the intensity of the light and the duration of exposure to the light are controlled such that a first portion (which can be a selected amount) of the complex is cleaved and a second portion of the complex remains intact. Put another way, the rate of cleavage or release of the antisense nucleobase polymer is controlled (i.e. a dose-response as a function of cumulative light energy). Furthermore, the irradiation step is optionally repeated until the all the complex is depleted.

Irradiation of the complex permits temporal control over modulation of a target mRNA. For example, the method includes exposing the cell containing the complex to light comprising a predetermined wavelength at a preselected time point during the development of a whole organism, where the cell is a subset of all cells in the whole organism.

As another example, in one class of embodiments, the complex comprises at least one label (e.g., one with a cleavage-dependent signal output), and the methods include detecting a signal from the label.

The disclosed method optionally includes introducing a plurality of complexes into the cell. The plurality of complexes is then photocleaved simultaneously or at different times. For example, a first complex is cleaved, such as by exposure to light of a first wavelength, and permitted to modulate a first target mRNA. A second complex is photocleaved, such as by exposure to light of a second, different wavelength, at a later time.

In another aspect, systems and/or apparatus comprising the compositions (e.g., the photocleavable sense-antisense complexes) noted above and components such as detectors, fluid handling apparatus, sources of light energy, or the like, are a feature of the disclosure.

In practicing the methods of the disclosure, many conventional techniques in molecular biology are optionally used (e.g., for making and/or manipulating nucleic acids, polypeptides, cells and organisms). These techniques are well known, and detailed protocols for numerous such procedures (including, in vitro amplification of nucleic acids, cloning, mutagenesis, transformation, cellular transduction with nucleic acids, protein expression, and/or the like) are described in, for example, Berger and Kimmel, *Guide to Molecular Cloning Techniques*, Methods in Enzymology volume 152 Academic Press, Inc., San Diego, Calif. (Berger); Sambrook et al., *Molecular Cloning: A Laboratory Manual* (3rd Ed.), Vol. 1-3, Cold Spring Harbor Laboratory, Cold Spring Harbor, N.Y., 2002 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002). Other useful references for cell isolation and culture (e.g., for subsequent nucleic acid or protein isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (Eds.) (1995) *Plant Cell, Tissue and Organ Culture; Fundamental Methods* Springer Lab Manual, Springer-Verlag (Berlin Heidelberg New York) and Atlas and Parks (Eds.) *The Handbook of Microbiological Media* (1993) CRC Press, Boca Raton, Fla.

I. Automated Systems

In another aspect, systems and/or an apparatus comprising the compositions noted above and, components such as detectors, fluid handling apparatus, sources of light comprising a predetermined wavelength, or the like, are a feature of the present disclosure.

In general, various automated systems are used to perform some or all of the method steps as noted herein. In addition to practicing some or all of the method steps herein, digital or analog systems, that is, comprising a digital or analog computer, can also control a variety of other functions such as a user viewable display (e.g., to permit viewing of where to target light or method results) and/or control of output features.

For example, certain of the methods described above are optionally implemented via a computer program or programs (such as, selectively modulating (e.g., attenuating) expression of a target mRNA in a cell containing a photocleavable sense-antisense complex (the 'complex') using targeted light irradiation). Thus, the present disclosure provides digital systems, e.g., computers, computer readable media, and/or integrated systems comprising instructions (e.g., embodied in appropriate software) for performing the methods herein. For example, one feature is a digital system comprising instructions for interpreting the change in signal output from the label to determine the extent of cleaved complex present in the cell and/or to determine the location of photocleavage in the cell or group of cells. The digital system optionally includes information (data) corresponding to x-y positions of irradiating regions and signal output intensities or the like. The system aids a user in performing photocleavage of the complex according to the disclosed methods herein, or can control laboratory equipment which automates introduction of the complex into the cells, detection of the signal outputs, or the like.

Standard desktop applications, such as word processing software (e.g., Microsoft Word® or Corel WordPerfect®) and/or database software (e.g., spreadsheet software such as Microsoft Excel®, Corel Quattro PrO®, or database programs such as Microsoft Access® or Paradox®) are adapted to the present disclosure by inputting data which is loaded into the memory of a digital system and performing an operation as noted herein on the data. For example, systems include the foregoing software having the appropriate x-y coordinate (e.g., irradiation locations) data, etc., e.g., used in conjunction with a user interface (e.g., a GUI in a standard operating system such as a Windows, Macintosh or LINUX system) to perform any analysis noted herein, or simply to acquire data (e.g., in a spreadsheet) to be used in the methods herein.

Systems typically include, e.g., a digital computer with software for performing signal output/input interpretation, or the like, as well as data sets entered into the software system comprising signal output intensities, x-y coordinates, or the like. The computer can be a PC (Intel x86 or Pentium chip-compatible DOS™, OS2™, WINDOWS™, WINDOWS NT™, WINDOWS 95™, WINDOWS 98™, WINDOWS XPT™, LINUX, Apple-compatible, MACINTOSH™ compatible, Power PC compatible, or a UNIX compatible (e.g., SUN™ work station) machine) or other commercially common computer. Software for performing analysis of signal output and/or mRNA quantitation is constructed using a standard programming language such as C++, Visualbasic, Fortran, Basic, Java, or the like, according to the methods herein.

Any system controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of irradiation coordinates (i.e., positions in the sample to be photocleaved), the wavelength, duration and intensity of irradiation or fluorescent emission to be monitored, or the like, in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operation. For example, in addition to performing signal output analysis, a digital system controls laboratory equipment for liquid handling, signal detection, or the like according to the relevant method herein.

Embodiments of the disclosure can also be embodied within the circuitry of an application specific integrated circuit (ASIC) or programmable logic device (PLD). In such a case, the embodiment is embodied in a computer readable descriptor language that is used to create an ASIC or PLD. The embodiment can also be embodied within the circuitry or logic processors of a variety of other digital apparatus, such as PDAs, laptop computer systems, displays, image editing equipment, etc.

J. Kits

Another aspect of the disclosure includes kits related to the methods. For example, one class of embodiments provides a kit for making a photocleavable sense-antisense nucleobase polymer complex, comprising a photocleavable sense nucleobase polymer and instructions for assembling the photocleavable sense nucleobase polymer and an antisense nucleobase polymer to form the photocleavable sense-antisense nucleobase polymer complex, packaged in one or more containers. The antisense nucleobase polymer is preferably an unnatural antisense nucleobase polymer that targets an mRNA. In some embodiments, the antisense nucleobase polymer may be provided in the kit or supplied by a user of the kit.

Another class of embodiments provides a kit for making the photocleavable sense-antisense nucleobase polymer complex, comprising a photocleavable monomer for assembly into a photocleavable sense nucleobase polymer, and instructions for assembling the photocleavable sense nucleobase polymer and an unnatural antisense nucleobase polymer to form the photocleavable sense-antisense nucleobase polymer complex, packaged in one or more containers.

In preferred embodiments the photocleavable monomer in the kit is a phosphoramidite suitable for use on convention automated synthesizers. In alternative embodiments, one or more of the other kit components (e.g., remaining monomers required for assembling the sense and/or antisense nucleobase polymers) are supplied in the kit, or are supplied by a user of the kit.

Kit instructions for the above embodiments can include, for example, instructions for the sequence of the antisense and sense nucleobase polymers, coupling conditions of any supplied phosphoramidite monomers, the annealing conditions to form the complex, the concentration of the complex to use in the cell for appropriate modulation of the target mRNA, the irradiation duration and intensity to achieve complete photocleavage, and the expected phenotype, if any, and the like.

All of the various optional configurations and features noted for the embodiments above apply here as well, to the extent they are relevant, e.g., for label configurations (e.g., use of fluorescent labels, fluorescent label/quencher, and donor/acceptor combinations), signal output types, nucleobase polymer configurations (e.g., various lengths, with or without overhangs, etc.), types of photolinkages (e.g., photolabile caging groups), appropriate irradiation conditions energies, use of cellular delivery modules (e.g., amphipathic peptides, cationic peptides, protein transduction domains, and lipids), and the like.

In addition, the kit optionally also includes at least one buffer and/or at least one delivery reagent. The delivery reagent can be essentially any reagent that can mediate introduction of the complex into the cell; for example, the delivery reagent can comprise a polypeptide or at least one lipid. In one class of embodiments, the kit optionally includes a control reagent (e.g. a tracer) for monitoring photocleavage efficiency (e.g., a caged fluorophore, e.g., caged FITC or caged dextran) and/or the naked antisense nucleobase polymer alone (e.g., to be used as a control to monitor photocleavage of the complex vs. maximal modulation of the target mRNA, and/or the like). The kit also optionally includes packaging or instructional materials for such additional reagents.

EXAMPLE 1

Modulating Expression by a Sense-Antisense Heteroduplex

The following sets forth a series of experiments that demonstrate the ability to modulate (i.e.; attenuation) the expression of a target mRNA in a cell using different ratios of sense and antisense nucleobase polymers. The antisense nucleobase polymer was a morpholino complementary to green fluorescent protein (GFP) and having the base sequence, AAGTTCTTCT CCTTTACTCA TGGTG [SEQ ID NO 1] (Gene Tools, LLC, Philomath, Oreg., www.gene-tools.com). The sense nucleobase polymer was an RNA lacking a photolabile linkage that was complementary to the morpholino base sequence, and thus had the base sequence, CAC-CAUGAGU AAAGGAGAAG AACUU [SEQ ID NO 2] (Integrated DNA Technologies, Inc., Coralville, Iowa, www.idtdna.com).

In an aqueous buffered solution containing 100 mM KCl, the antisense nucleobase polymer at a final concentration of 10 µM was combined with variable amounts of the sense nucleobase polymer to yield the molar ratios given in Table 1. Annealing of the two polymers into a heteroduplex was performed by heating the mixture to 70° C. for 20 minutes in a hybridization oven, then cooling to 4° C. overnight.

TABLE 1

Expression of GFP in zebrafish microinjected with a sense-antisense heteroduplex

| Experiment | Ratio of antisense:sense* | Normalized fluorescence** |
|---|---|---|
| 1 | uninjected control | 100 |
| 2 | 1:0 | 0 |
| 3 | 1:1.5 | 16.7 |
| 4 | 1:5 | 24.8 |
| 5 | 1:10 | 73.6 |

*Morpholino: RNA.
**Expressed as % of uninjected control minus background.

Heteroduplexes derived from the indicated ratios of antisense and sense nucleobase polymers were microinjected in 5 nL into 1-2 cell stage transgenic zebrafish embryos that expressed GFP in digestive organs (i.e., GutGFP zebrafish). An uninjected control served to define the maximum GFP expression in the zebrafish. At 48 hours post fertilization, zebrafish embryos were scored for GFP fluorescence using a stereomicroscope. Fluorescence intensity was quantified for individual embryos by measuring the intensity at the brightest point on the embryo. At least 25 independent measurements were made for the uninjected control (experiment 1) and each of the ratios of antisense-to-sense nucleobase polymers (experiments 2-5). Normalized fluorescence intensity was then expressed as a mean of the percent of control (uninjected) minus background.

These data demonstrate that a sense RNA can modulate (attenuate) the knock-down activity exerted by an antisense morpholino complementary to a target GFP mRNA. A sense-to-antisense nucleobase polymer ratio of 5:1 or greater was required to restore GFP mRNA expression to at least 25% of that obtained in the uninjected control (see Table 1). A sense-to-antisense nucleobase polymer ratio of 10:1 resulted in GFP mRNA expression that approached the uninjected control.

Modulating Expression by a Photolabile Sense-Antisense Complex

The following sets forth a series of experiments that demonstrate use of a photolabile sense-antisense complex to control mRNA (GFP) expression in the cells of a whole zebrafish using targeted light irradiation of a predetermined wavelength. As above, the antisense nucleobase polymer was again the morpholino complementary to the green fluorescent protein (GFP) and having the base sequence, AAGTTCTTCT CCTTTACTCA TGGTG [SEQ ID NO 3] (Gene Tools, LLC, Philomath, Oreg., www.gene-tools.com). Three different photolabile sense nucleobase polymers were prepared comprising two segments of RNA connected via photolabile linkage I (see section C. Photocleavable Sense Nucleobase Polymer above) as follows,

```
STX2: CAC CAU GAG UAA XAG GAG AAG AAC UU,

STX4: CAC CAU GAG UAA X_G GAG AAG AAC UU,
and

STX6: CAC CAU GAG UA— X_G GAG AAG AAC UU,
where,
X = photolabile linkage 1 and underscore denotes
base removed relative to STX2 base sequence.
```

The photolabile sense nucleobase polymers were prepare by Trilink Biotechnologies, Inc. (San Diego, Calif., www.trilinkbiotech.com) using the commercially available photocleavable phosphoramidite 3-(4,4'-Dimethoxytrityl)-1-(2-nitrophenyl)-propan-1-yl-[(2-cyanoethyl)-(N,N-diisopropyl)]-phosphoramidite (PC Linker from Glen Research, Sterling, Va., www.glenres.com).

The photolabile sense-antisense complex was formed for each of the photolabile sense nucleobase polymers STX2, STX4 and STX6 by separately combining the photolabile sense nucleobase polymer (100 µM) with the morpholino antisense nucleobase polymer (10 µM) in a buffered aqueous solution containing 100 mM KCl and heating the mixture to 70° C. for 20 minutes in a hybridization oven, followed by cooling to 4° C. overnight. All manipulations were performed under reduced ambient light.

TABLE 2

Expression of GFP in zebrafish microinjected with a photolabile sense-antisense complex

| Experiment | Antisense nucleobase polymer | Sense nucleobase polymer | Not irradiated* | Irradiated* |
|---|---|---|---|---|
| 6** | none | none | 100 | 98.2 |
| 7 | morpholino | none | 0 | 0 |
| 8 | morpholino | STX2 | 113 | 29.7 |
| 9 | morpholino | STX4 | 73.7 | 7.1 |
| 10 | morpholino | STX6 | 64.8 | 17.9 |

*Expressed as % of uninjected control minus background.
**Uninjected control.

Each of the formed photolabile sense-antisense complexes and the morpholino antisense nucleobase polymer control were microinjected in 5 nL into 1-2 cell stage GutGFP zebrafish embryos. An uninjected control served to define the maximum GFP expression in the zebrafish. A yellow filter was used to reduce short wavelength light during the injections. Irradiation at the predetermined photocleavage wavelength was performed 4-6 hours post-injection by exposing the embryos to UV light (365 nm, 0.16 amps, UVL-56 lamp, UVP, Upland, Calif.) at a distance of 10 cm for a period of 30 minutes, with swirling of the plate every 10 min to ensure uniform irradiation.

At 48 hours post fertilization, zebrafish embryos were scored for GFP fluorescence using a stereomicroscope (see Table 2). Fluorescence intensity was quantified for individual embryos by measuring the intensity at the brightest point on the embryo. At least 25 independent measurements were made for the uninjected control (experiment 6), the antisense nucleobase polymer only control (experiment 7), and each of the photolabile sense-antisense complexes (experiments 8-10). Normalized fluorescence intensity was then expressed as a mean of the percent of control (uninjected) minus background.

These data demonstrate that all three unirradiated photolabile sense nucleobase polymers (STX2, STX4 and STX6) modulated (i.e., attenuated) the knock-down activity exerted by the antisense morpholino nucleobase polymer, giving GFP expression comparable to uninjected zebrafish. Irradiation of the zebrafish embryos early in development however, restored 70-93% of the knock-down activity of the antisense morpholino (see Table 2).

Thus, modulation of the target mRNA (GFP mRNA) has been achieved by exposing the animal containing the complex to light of a predetermined wavelength (i.e., antisense activity was 'off' in the absence of light, with targeted irradiation turning antisense activity 'on'). Again, not wishing to be bound by theory, irradiation at the predetermined wavelength presumably cleaved the photolabile sense nucleobase polymer in the complex and freed the antisense nucleobase polymer, thereby permitting it to bind the target GFP mRNA.

EXAMPLE 2

Figure 2:
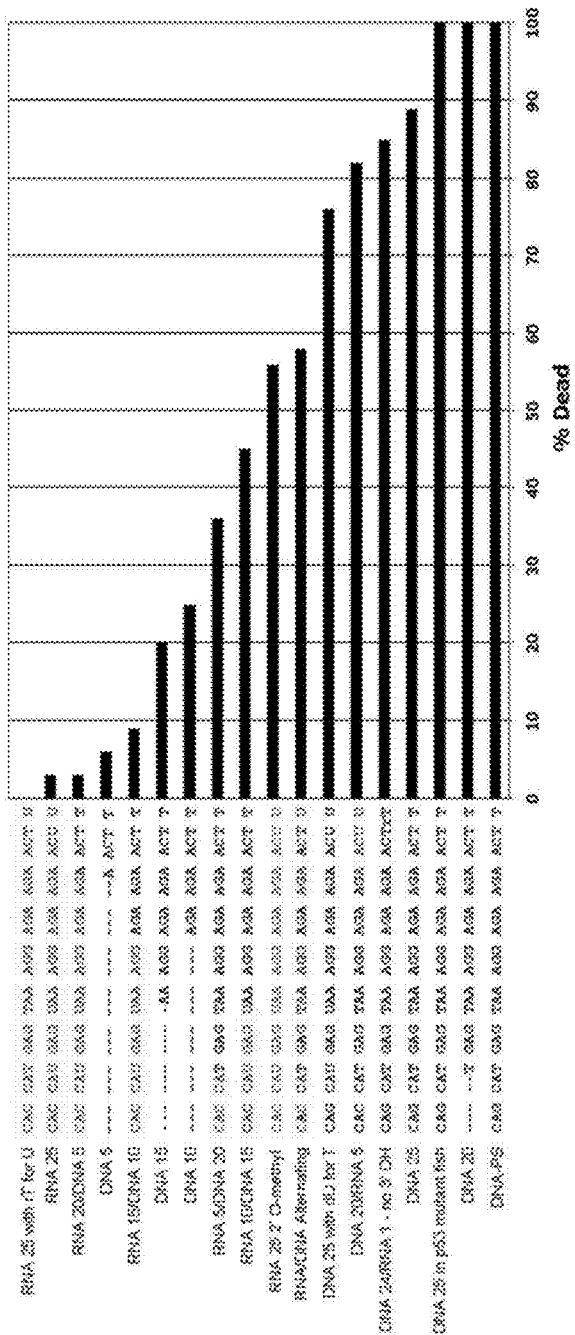
FIG. 2 shows that there was found greater toxicity with increasing DNA content. A 10-mer of DNA without RNA in the backbone killed 25% of the embryos. However, if RNA makes up the rest of the backbone, 10 DNA bases were not as toxic, killing less than 10% of the embryos. Most importantly, backbones comprised entirely of RNA were the least toxic. Addition of DNA to the backbone increased toxicity, and this result was more severe when RNA is removed from the backbone. Each oligo was injected at 100 µM and embryos screened for toxicity at 24 hpf.

This example shows that conventional morpholinos can be converted into conditional knockdown reagents by hybridization to a complementary oligonucleotide strand containing a photocleavable linker. A wide variety of caging backbones using the same morpholino were tested. Caging strands were generated consisting of many variations on the phosphoribose backbone, including all DNA, RNA, DNA deletions, RNA deletions, alternating RNA and DNA, varying percentages of RNA and DNA in different orientations, substituting ribothymidine for ribouridine in the RNA backbone, and substituting deoxyuridine for deoxythymidine in the DNA backbone. There are also tried variations on the normal linkages, including no 3' OH group, the addition of a 2' O-methyl group, and a phosphorothioate linkage in the DNA backbone. Each oligo was injected at 100 µM and embryos screened for toxicity at 24 hpf (FIG. 2). In general, there was found greater toxicity with increasing DNA content. A 10-mer of DNA without RNA in the backbone killed 25% of the embryos. However, if RNA makes up the rest of the backbone, 10 DNA bases were not as toxic, killing less than 10% of the embryos. Most importantly, backbones comprised entirely of RNA were the least toxic. Addition of DNA to the backbone increased toxicity, and this result was more severe when RNA is removed from the backbone.

Caging strands were generated with standard solid phase oligonucleotide synthesis (SuperNova Life Science, www.supernovalifescience.com). The photocleavable nitrophenyl group was introduced as a phosphoramidite during synthesis. Caging strands were injected into the yolk of the 1-cell stage embryo at 100 µM (4.6 nL per injection), using a Drummond Nanoject II microinjector. Embryos were scored for death at 24 hpf.

To generate PhotoMorphs, caging strands were hybridized to morpholinos by incubation at 70° C. for 30 minutes in Danieau's solution (Westerfield, editor. 1995. *The Zebrafish Book,* 3rd ed. Eugene: The University of Oregon Press.) and phenol red (0.1%), followed by slow cooling and storage at 4° C. overnight. Molar ratios were typically 1:8-1:10 as indicated. Mixes were injected into the yolk of a 1-cell stage embryo (4.6 nL per injection). PhotoMorphs are light sensitive, therefore all work was done under reduced lighting conditions, and injections were performed using a yellow filter to prevent photocleavage during injection. Embryos were irradiated with 365 nm light using a UVL-56 UV lamp at a distance of 5 cm, which delivered 1350 µW/cm$^2$ per manufacturer's specifications. Irradiation is performed at various time-points for 30 minutes, with periodic swirling of the plate to ensure uniform irradiation. This delivered 2.43 J/cm$^2$ of UVA radiation, which is below the measured LD$_{50}$ of 850 J/cm$^2$ UVA as described previously (Dong et al., *J, Photochem. Photobiol.* B 88:137-146, 2007). UV treatment alone had no detectable adverse effects on development, consistent with previous reports. Embryos were imaged for data analysis at various time-points.

To quantify the efficacy of the GFP PhotoMorph, Adobe Photoshop was used to pinpoint the brightest point of fluorescence in the embryo (GutGFP transgenic line, Zebrafish International Resource Center, www.zebrafish.org). The average luminosity was calculated within a clutch of treated embryos and then normalized the values relative to the control (1) and the morpholino knockdown (0) to graph relative GFP expression. The efficacy of the ntl PhotoMorph at 79 hpf was determined by grouping the embryos within each condition according to severity of the ntl phenotype. The number of embryos was counted in each phenotype group to express ntl PhotoMorph efficacy as a percentage. Canvas X was used to score the phenotype at 27 hpf to measure the length of the embryo, from head to tail. The embryos were grouped to determine the efficacy of the E-cadherin PhotoMorph at 24 hpf within each condition according to severity of cdhl knockdown phenotype. The number of embryos was counted in each phenotype group to express E-cadherin PhotoMorph efficacy as a percentage.

Experiments were performed using embryos from the same clutch for all conditions within each experiment.

For western blotting, about 20 embryos were homogenized in 200 µL of 2×SDS sample buffer containing a cocktail of protease inhibitors (Roche, catalog #11836170001, www.roche-applied-science.com) and then sonicated the samples 2 times for 30 seconds. Samples were boiled, spun down, and frozen for Western blot analysis. Samples were loaded on a 7.5% gel for SDS-PAGE, and then transferred to PVDF. An E-cadherin mouse monoclonal antibody (BD Transduction Laboratories, catalog #610181, www.bdbiosciences.com) at 1:2500 in 5% milk was used. The blot was stripped using Restore Western Blot Stripping Buffer (Pierce, www.piercenet.com), then re-probed using mouse monoclonal β-Actin antibody [AC-15] (Abcam, catalog #ab6276, www.abcam.com). HRP-conjugated secondary antibodies were used at 1:15,000 and blots were developed using Super-Signal West Pico Chemiluminescent Substrate (Pierce, www.piercenet.com) according to the manufacturer's protocol. Densitometry was performed using Scion Image 1.63 to measure band density in a fixed area, subtracted background signal and normalized to actin.

RNA was collected and RT-PCR done from RNA collected from 10 embryos per condition using TRIzol, according to the manufacturer's protocol (Invitrogen, www.invitrogen.com). Reverse transcription reactions were performed using oligo (dT)20 primers and SuperScript™ II, according to the manufacturer's protocol (Invitrogen). Primer sequences were: rheb-f: GGGG ACA AGT TTG TAC AAA AAA GCA GGC TCC ATG CCG CAG CCG AAA TCG C [SEQ ID NO 4], rheb-rev: GGGG AC CAC TTT GTA CAA GAA AGC TGG GTC CAT CAT GGA GCA GGG CGT C [SEQ ID NO 5], ef1α-f: CTTCTCAGGCTGACTGTGC [SEQ ID NO 6], ef1α-rev: CCGCTAGCATTACCCTCC [SEQ ID NO 7]. An RT-PCR program: 94° C. for 3 min, 94° C. for 30 sec, 58° C. for 30 sec, 72° C. for 1 min, 34 times to step 2, 72° C. for 10 min, and hold at 4° C. was used.

Figure 3:
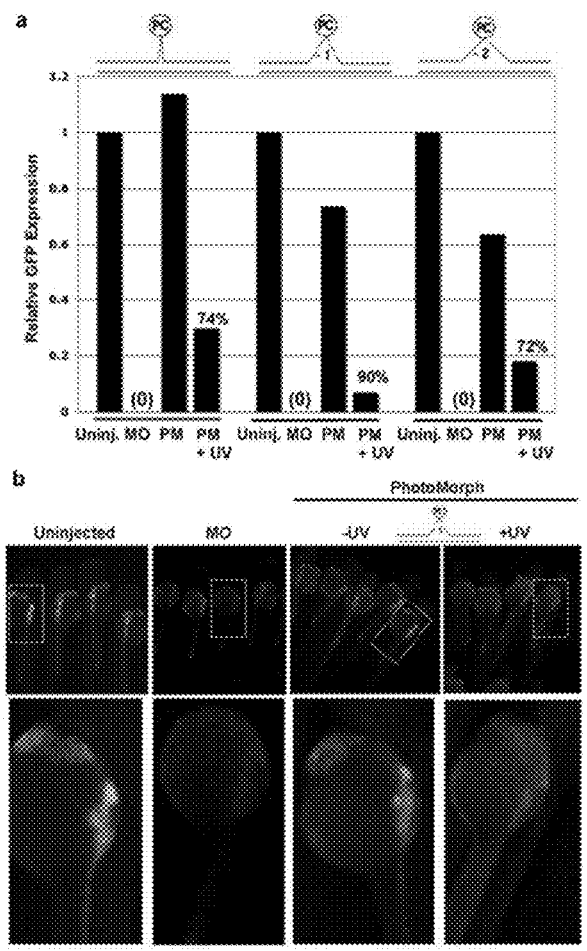
FIG. 3 shows that embryos injected with the PhotoMorph were indistinguishable from the uninjected group, demonstrating the effectiveness of the caging. After uncaging, many embryos became severely affected, while others develop relatively normally. The phenotype varied as a function of the stage of uncaging, with milder effects the later the uncaging was performed, consistent with the role of ntl early in development. Scoring the knockdown phenotype at 27 hpf produced a similar result. The embryos were divided in each condition into groups according to phenotypic severity.

Other geners were tested genes using a similar algorithm to Example 1: first identifying the lowest concentration of morpholino that gives acceptable knockdown, then generating the PhotoMorph by hybridizing a molar excess of caging strand. A no tail gene was chosen because of the clear phenotype produced by its knockdown (Halpern et al., *Cell* 75:99-111, 1993). ntl morpholino was injected ranging from 12.5 μM to 100 μM, and found that 12.5 μM was sufficient to produce adequate knockdown and a strong phenotype. Without being bound by theory, the morpholino (12.5 μM) with the caging strand (100 μM) generated the ntl PhotoMorph. The PhotoMorphs were uncaged at various timepoints and scored the embryos at 79 hpf. The embryos were divided in each condition into groups according to phenotypic severity (FIG. 3). Embryos injected with the PhotoMorph were indistinguishable from the uninjected group, demonstrating the effectiveness of the caging. After uncaging, many embryos became severely affected, while others develop relatively normally. The phenotype varied as a function of the stage of uncaging, with milder effects the later the uncaging was performed, consistent with the role of ntl early in development. Scoring the knockdown phenotype at 27 hpf produced a similar result.

Figure 4:
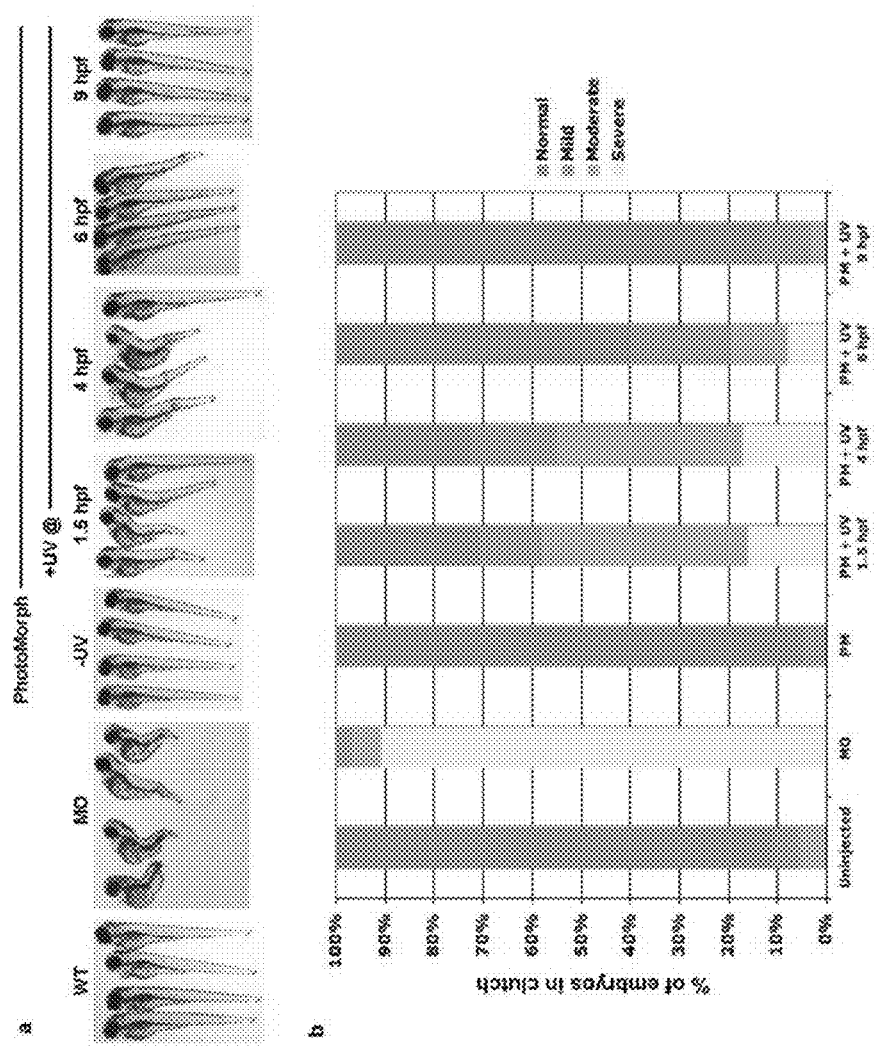
FIG. 4 shows that morpholino concentrations ranging from 1 µM to 100 µM were tested. At concentrations of 10 µM and above, most embryos died by 24 hpf. Below 10 µM, the majority of embryos were unaffected. 10 µM morpholino and 100 µM caging strand were used to generate the PhotoMorph. Clutches were scored by sorting embryos into groups according to phenotypic severity, including normal, mildly deformed (presence of head and tail), severely deformed (absence of head and tail), and dead. Although variable morpholino efficacy between clutches was observed, only 6% of the PhotoMorph-injected embryos were dead at 24 hpf. For both clutches, the percent of affected embryos was similar between the unmodified and uncaged morpholino, (84% and 90% uncaging efficiency for clutch 1 and 2, respectively).

A PhotoMorph directed to the cdhI gene, which encodes E-cadherin was next tested. This knockdown phenotype features gastrulation defects and mimics the half-baked mutant (Kane et al., *Development* 132:1105-1116, 2005). Morpholino concentrations ranging from 1 μM to 100 μM were tested. At concentrations of 10 μM and above, most embryos died by 24 hpf. Below 10 μM, the majority of embryos were unaffected. 10 μM morpholino and 100 μM caging strand were used to generate the PhotoMorph. Clutches were scored by sorting embryos into groups according to phenotypic severity, including normal, mildly deformed (presence of head and tail), severely deformed (absence of head and tail), and dead (FIG. 4). Although variable morpholino efficacy between clutches was observed, only 6% of the PhotoMorph-injected embryos were dead at 24 hpf (FIG. 4). For both clutches, the percent of affected embryos was similar between the unmodified and uncaged morpholino, (84% and 90% uncaging efficiency for clutch 1 and 2, respectively).

In three separate experiments, there were uncaged at pre- and post-gastrulation time-points (4 hpf and 8 hpf, respectively). On average, only 4% of PhotoMorph injected embryos were dead at 24 hpf. Uncaging at 4 hpf resulted in death of an average of 36% of the embryos, while uncaging at 8 hpf resulted in death of 10% of the embryos, illustrating stage-specific knockdown. This result demonstrates the ability to circumvent early lethal phenotypes by controlling the timing of PhotoMorph activation.

Figure 5:
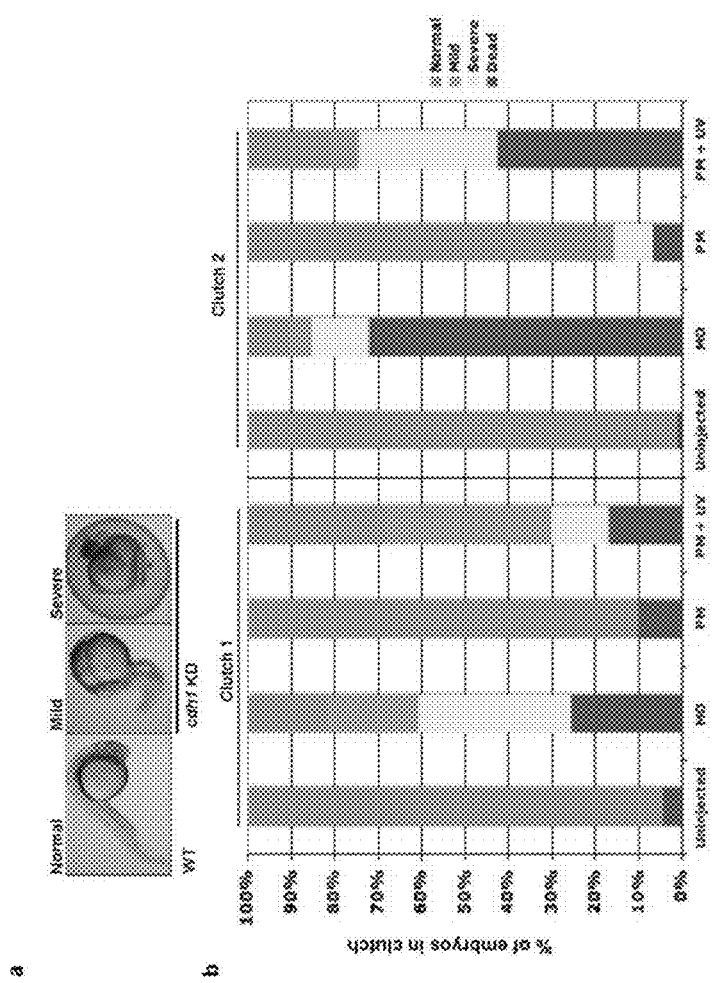
FIG. 5 shows Western blotting to compare morpholino (10 µM) with caged and uncaged PhotoMorph (10 µM morpholino and 100 µM caging strand) in order to quantify the effectiveness of the E-cadherin PhotoMorph. At 2 time-points (8 hpf raised at 28° C. and 24 hpf raised at room temperature, indicated by asterisk), the unmodified and the uncaged morpholinos gave comparable knockdown, and the caged morpholino was comparable to uninjected control. However, there was observed better knockdown for both morpholino and uncaged PhotoMorph at 24 hpf*, likely due to the time needed for decay of preexisting protein. Using higher concentrations of morpholino (20 µM) and PhotoMorph (20 µM morpholino and 200 µM caging strand) resulted in better conventional morpholino knockdown, but less effective caging and uncaging.

In order to quantify the effectiveness of the E-cadherin PhotoMorph, Western blotting to compare morpholino (10 μM) with caged and uncaged PhotoMorph (10 μM morpholino and 100 μM caging strand) was performed (FIG. 5). At 2 time-points (8 hpf raised at 28° C. and 24 hpf raised at room temperature, indicated by asterisk), the unmodified and the uncaged morpholinos gave comparable knockdown, and the caged morpholino was comparable to uninjected control. However, there was observed better knockdown for both morpholino and uncaged PhotoMorph at 24 hpf* (FIG. 5), likely due to the time needed for decay of preexisting protein. Using higher concentrations of morpholino (20 μM) and PhotoMorph (20 μM morpholino and 200 μM caging strand) resulted in better conventional morpholino knockdown, but less effective caging and uncaging.

Figure 6:
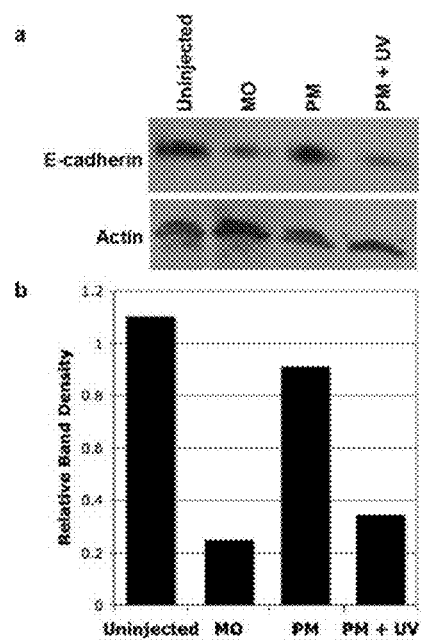
FIG. 6 shows a splice inhibiting PhotoMorph that was used directed to the rheb gene to monitor the time course for uncaging by RT-PCR. At 100 µM, acceptable knockdown with minimal toxicity at 24 hpf was achieved. The PhotoMorph was generated by hybridizing 100 µM morpholino to 500 µM caging strand, and found to be effective caging at 30 hpf and 54 hpf. At later time-points caging was detectable, but less robust.

For a splice inhibiting PhotoMorph, a PhotoMorph was used directed to the rheb gene to monitor the time course for uncaging by RT-PCR. At 100 μM, acceptable knockdown with minimal toxicity at 24 hpf was achieved. The PhotoMorph was generated by hybridizing 100 μM morpholino to 500 μM caging strand, and found to be effective caging at 30 hpf and 54 hpf. At later time-points caging was detectable, but less robust (FIG. 6).

Uncaging rheb PhotoMorph by UV irradiation at 24, 48 and 72 hpf was tested and collected RNA 6 hours post-irradiation. Excellent UV-dependent knockdown of rheb at 24 and 48 hpf was detected. At 72 hpf, UV-induced gene knockdown was detectable but less pronounced due to less efficient caging One explanation for this observation is a dilution-driven dissociation of the PhotoMorph heteroduplex at later stages of development.

These data nonetheless demonstrate the feasibility of using PhotoMorphs to defer the temporal window of knockdown relative to conventional morpholinos, a long sought-after capability.

EXAMPLE 3

There are many applications for PhotoMorphs. Examples 1 and 2 identified variables for optimal caging and uncaging, including morpholino concentration, the chemical composition of the caging strand, and the molar ratio of morpholino to caging strand. Caging strands can be synthesized for virtually any morpholino sequence, circumventing the need for a specialized hairpin that is not commercially available as of this writing.

The main application of PhotoMorph technology is spatial and temporal gene regulation. Researchers can use PhotoMorphs to control timing of gene knockdown, delaying morpholino activation until a specified time in development. For example, uncaging after gastrulation can produce a morphant phenotype that would have otherwise been inaccessible due to early lethality caused by pre-gastrulation knockdown.

While the foregoing invention has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

I claim:

1. A photocleavable sense-antisense nucleobase polymer complex capable of modulating gene expression, comprising an unnatural non-photocleavable antisense nucleobase polymer that targets an mRNA, and a photocleavable sense nucleobase polymer noncovalently bound to the antisense nucleobase polymer, wherein the photocleavable sense nucleobase polymer comprises a a centrally placed photocleavable linkage, wherein the photocleavable linkage does not block the activity of the activity of the antisense nucleobase polymer, wherein upon light irradiation the photocleavable linkage moiety cleaves and bisects the sense nucleobase polymer into two halves, wherein the binding stability of the two halves of the sense cleaved nucleobase polymer is significantly reduced relative to that of the intact sense nucleobase polymer, wherein upon cleavage the two halves of the sense nucleobase polymer dissociate from and release the antisense nucleobase polymer, and wherein the released antisense nucleobase polymer initiates knockdown of the target mRNA.

2. The photocleavable sense-antisense nucleobase polymer complex of claim 1, wherein the photocleavable linkage further comprises a nitro group attached to an aromatic group.

3. The photocleavable sense-antisense nucleobase polymer complex of claim 1, wherein the photocleavable linkage comprises a coumarin group.

4. The photocleavable sense-antisense nucleobase polymer complex of claim 1, wherein the photocleavable sense nucleobase polymer further comprises a second photocleavable linkage.

5. The photocleavable sense-antisense nucleobase polymer complex of claim 1, further comprising a label.

6. The photocleavable sense-antisense nucleobase polymer complex of claim 5, wherein the label is selected from the group consisting of quantum dots, hydrophobic fluorophores, coumarin, rhodamine, fluorescein, radionucleotides, enzymes, substrates, cofactors, inhibitors, fluorescent moieties, chemiluminescent moieties, magnetic particles, donor/acceptor and fluorophore/quencher combinations, fluorescence resonance energy transfer (FRET)-based quenching, non-FRET based quenching, or wavelength-shifting harvester molecules terbium chelate and TRITC (tetrarhodamine isothiocyanate), lanthanide (e.g., europium or terbium) chelates and allophycocyanin (APC) or Cy5, europium cryptate and allophycocyanin, fluorescein and tetramethylrhodamine, IAEDANS and fluorescein, EDANS and DABCYL, fluorescein and DABCYL, fluorescein and fluorescein, BODIPY FL and BODIPY FL, fluorescein and QSY 7 dye, nonfluorescent acceptors, DABCYL and QSY 7 and QSY 33 dyes, and combinations thereof.

7. The photocleavable sense-antisense nucleobase polymer complex of claim 1, wherein the unnatural antisense non-photocleavable nucleobase polymer comprises a nucleobase analog consisting of morpholino, PNA, ncPNA, LNA, 2'-OMe-RNA and 2'-OMe- DNA.

8. The photocleavable sense-antisense nucleobase polymer complex of claim 1, wherein the photocleavable sense nucleobase polymer is partially complementary to the antisense nucleobase polymer.

9. The photocleavable sense-antisense nucleobase polymer complex of claim 1, wherein the photocleavable sense nucleobase polymer is substantially complementary to the antisense nucleobase polymer.

10. The photocleavable sense-antisense nucleobase polymer complex of claim 1, wherein the antisense nucleobase polymer is substantially complementary to the target mRNA.

11. The photocleavable sense-antisense nucleobase polymer complex of claim 1, wherein the antisense nucleobase polymer and the photocleavable sense nucleobase polymer are each 20-30 nucleobases.

* * * * *